(12) United States Patent
Schmitt

(10) Patent No.: US 8,364,301 B2
(45) Date of Patent: Jan. 29, 2013

(54) SURGICAL GUIDES AND METHODS FOR POSITIONING ARTIFICIAL TEETH AND DENTAL IMPLANTS

(75) Inventor: Stephen M. Schmitt, San Antonio, TX (US)

(73) Assignee: Bankruptcy Estate of Voxelogix Corporation, San Antonio, TX (US)

( * ) Notice: Subject to any disclaimer, the term of this patent is extended or adjusted under 35 U.S.C. 154(b) by 121 days.

(21) Appl. No.: 12/947,698

(22) Filed: Nov. 16, 2010

(65) Prior Publication Data

US 2011/0066267 A1   Mar. 17, 2011

Related U.S. Application Data

(62) Division of application No. 11/867,590, filed on Oct. 4, 2007, now Pat. No. 7,835,811.

(60) Provisional application No. 60/849,994, filed on Oct. 7, 2006.

(51) Int. Cl.
*G06F 19/00* (2011.01)
(52) U.S. Cl. .................... 700/118; 700/98; 700/119
(58) Field of Classification Search .............. 700/98, 700/118, 119
See application file for complete search history.

(56) References Cited

U.S. PATENT DOCUMENTS

| | | | |
|---|---|---|---|
| 4,208,794 A | 6/1980 | Gerber | |
| 4,226,592 A | 10/1980 | Schreinemakers | |
| 4,234,307 A | 11/1980 | Draheim | |
| 4,575,805 A | 3/1986 | Moermann et al. | |
| 4,615,678 A | 10/1986 | Moermann et al. | |
| 4,616,998 A | 10/1986 | Wong | |
| 4,766,704 A | 8/1988 | Brandestini et al. | |
| 4,795,345 A | 1/1989 | Ai et al. | |
| 4,837,732 A | 6/1989 | Brandestini et al. | |
| 4,859,181 A | 8/1989 | Neumeyer | |
| 4,901,737 A | 2/1990 | Toone | |
| 5,090,047 A | 2/1992 | Angotti et al. | |
| 5,237,998 A | 8/1993 | Duret et al. | |
| 5,257,203 A | 10/1993 | Riley et al. | |

(Continued)

FOREIGN PATENT DOCUMENTS

GB   2440267 A   1/2008
JP   2010142491 A * 7/2010

(Continued)

OTHER PUBLICATIONS

Schmitt, The 3rd Annual Eugene C. Gwaltney Manufacturing Symposium, "Rapid Prototyping for Product Development, Design, and Tooling: Making the New Technologies Pay Off for You" "Changing Peoples' Lives with RPM",Oct. 1-3, 1996, pp. 75-83 (10 pages).

(Continued)

*Primary Examiner* — Michael D Masinick
(74) *Attorney, Agent, or Firm* — Cox Smith Matthews Incorporated

(57) ABSTRACT

A method is set forth for making a computer model of patient's jaws on the basis of digital information. Digital data about the jaws, teeth, soft tissues and artificial teeth is joined in computer space to create aesthetic and functional plans for the removal of teeth, shaping of supporting bone and placement of dental implants. Artificial teeth and pre-manufactured prosthetic devices are made and attached to the dental implants at the time of surgery. The aesthetic and functional position of artificial teeth is determined prior to surgical removal of natural teeth and the ideal position of implants and the proper form of the remaining bone are determined prior to surgery. Surgical guides used to shape bone, record occlusal orientation and position dental implants are manufactured using computer milling or layered manufacturing.

8 Claims, 18 Drawing Sheets

U.S. PATENT DOCUMENTS

| | | | |
|---|---|---|---|
| 5,409,017 A | 4/1995 | Lowe | |
| 5,501,598 A | 3/1996 | Misch | |
| 5,527,182 A | 6/1996 | Willoughby | |
| 5,588,430 A | 12/1996 | Bova et al. | |
| 5,605,459 A | 2/1997 | Kuroda et al. | |
| 5,652,709 A | 7/1997 | Andersson et al. | |
| 5,662,476 A | 9/1997 | Ingber et al. | |
| 5,690,843 A | 11/1997 | Schmitt et al. | |
| 5,697,997 A | 12/1997 | Aronsson et al. | |
| 5,725,378 A | 3/1998 | Wang | |
| 5,733,126 A | 3/1998 | Andersson et al. | |
| 5,741,215 A | 4/1998 | D'Urso | |
| 5,768,134 A * | 6/1998 | Swaelens et al. | 700/121 |
| 5,779,477 A | 7/1998 | Boss | |
| 5,800,174 A | 9/1998 | Andersson | |
| 5,807,102 A | 9/1998 | Lang et al. | |
| 5,816,810 A | 10/1998 | Antonson et al. | |
| 5,823,778 A | 10/1998 | Schmitt et al. | |
| 5,829,981 A | 11/1998 | Ziegler | |
| 5,851,115 A | 12/1998 | Carlsson et al. | |
| 5,857,853 A | 1/1999 | van Nifterick et al. | |
| 5,868,138 A | 2/1999 | Halstrom | |
| 5,871,358 A | 2/1999 | Ingber et al. | |
| 5,880,962 A | 3/1999 | Andersson et al. | |
| 5,885,077 A | 3/1999 | Jeffer | |
| 5,938,446 A | 8/1999 | Andersson et al. | |
| 5,951,289 A | 9/1999 | Kura et al. | |
| 5,967,777 A | 10/1999 | Klein et al. | |
| 5,971,760 A | 10/1999 | Letcher | |
| 5,975,893 A | 11/1999 | Chishti et al. | |
| 5,989,029 A | 11/1999 | Osorio et al. | |
| 5,993,214 A | 11/1999 | Persson | |
| 6,015,289 A | 1/2000 | Andreiko et al. | |
| 6,049,743 A | 4/2000 | Baba | |
| 6,055,986 A | 5/2000 | Meade | |
| 6,062,860 A | 5/2000 | Jorgenson | |
| 6,066,274 A | 5/2000 | Antonson et al. | |
| 6,082,995 A | 7/2000 | Wise | |
| 6,126,445 A | 10/2000 | Willoughby | |
| 6,149,433 A | 11/2000 | Ziegler et al. | |
| 6,152,731 A | 11/2000 | Jordan et al. | |
| 6,155,828 A | 12/2000 | Lazzara et al. | |
| 6,159,010 A | 12/2000 | Rogers et al. | |
| 6,168,435 B1 | 1/2001 | Beaty et al. | |
| 6,186,790 B1 | 2/2001 | Karmaker et al. | |
| 6,210,162 B1 | 4/2001 | Chishti et al. | |
| 6,217,325 B1 | 4/2001 | Chishti et al. | |
| 6,217,331 B1 | 4/2001 | Rogers et al. | |
| 6,223,067 B1 | 4/2001 | Vilsmeier et al. | |
| 6,227,851 B1 | 5/2001 | Chishti et al. | |
| 6,231,342 B1 | 5/2001 | Osorio et al. | |
| 6,261,098 B1 | 7/2001 | Persson | |
| 6,276,938 B1 | 8/2001 | Jorneus et al. | |
| 6,283,752 B1 | 9/2001 | Kumar | |
| 6,287,116 B2 | 9/2001 | Lazzara | |
| 6,287,119 B1 | 9/2001 | van Nifterick et al. | |
| 6,296,483 B1 | 10/2001 | Champelboux | |
| 6,302,686 B1 | 10/2001 | Chott et al. | |
| 6,305,939 B1 | 10/2001 | Dawood | |
| 6,319,006 B1 | 11/2001 | Scherer et al. | |
| 6,322,359 B1 | 11/2001 | Jordan et al. | |
| 6,343,930 B1 | 2/2002 | Beaty et al. | |
| 6,354,836 B1 | 3/2002 | Panzera et al. | |
| 6,361,318 B1 | 3/2002 | Back et al. | |
| 6,382,975 B1 | 5/2002 | Poirier | |
| 6,394,801 B2 | 5/2002 | Chishti et al. | |
| 6,409,504 B1 | 6/2002 | Jones et al. | |
| 6,419,489 B1 | 7/2002 | Jorneus et al. | |
| 6,419,491 B1 | 7/2002 | Ricci et al. | |
| 6,431,866 B2 | 8/2002 | Hurson | |
| 6,463,344 B1 | 10/2002 | Pavloskaia et al. | |
| 6,491,723 B1 | 12/2002 | Beaty | |
| 6,505,625 B1 | 1/2003 | Uenishi | |
| 6,524,106 B1 | 2/2003 | Ziegler | |
| 6,530,375 B1 | 3/2003 | Cieslik, Jr. | |
| 6,540,516 B1 | 4/2003 | Ziegler | |
| 6,558,162 B1 | 5/2003 | Porter et al. | |
| 6,582,931 B1 | 6/2003 | Kois et al. | |
| 6,607,386 B1 | 8/2003 | Andersson et al. | |
| 6,621,491 B1 | 9/2003 | Baumrind et al. | |
| 6,633,789 B1 | 10/2003 | Nikolskiy et al. | |
| 6,640,150 B1 | 10/2003 | Persson et al. | |
| 6,648,645 B1 | 11/2003 | MacDougald et al. | |
| 6,652,765 B1 | 11/2003 | Beaty | |
| 6,655,962 B1 | 12/2003 | Kennard | |
| 6,665,570 B2 | 12/2003 | Pavloskaia et al. | |
| 6,671,539 B2 | 12/2003 | Gateno et al. | |
| 6,705,863 B2 | 3/2004 | Phan et al. | |
| 6,726,478 B1 | 4/2004 | Isiderio et al. | |
| 6,767,208 B2 | 7/2004 | Kaza | |
| 6,820,623 B2 | 11/2004 | Cook | |
| 6,886,566 B2 | 5/2005 | Eubank | |
| 6,935,861 B2 | 8/2005 | Lauciello | |
| 6,947,038 B1 | 9/2005 | Anh et al. | |
| 6,948,936 B2 | 9/2005 | Miller et al. | |
| 7,047,978 B2 | 5/2006 | Zuk | |
| 7,080,979 B2 | 7/2006 | Rubbert et al. | |
| 7,110,844 B2 | 9/2006 | Kopelman et al. | |
| 7,153,135 B1 | 12/2006 | Thomas | |
| 7,267,549 B2 | 9/2007 | Monkmeyer | |
| 7,286,954 B2 | 10/2007 | Kopelman et al. | |
| 7,322,824 B2 | 1/2008 | Schmitt | |
| 7,333,874 B2 | 2/2008 | Taub et al. | |
| 7,346,417 B2 | 3/2008 | Luth et al. | |
| 7,383,094 B2 | 6/2008 | Kopelman et al. | |
| 7,403,830 B2 | 7/2008 | Weber et al. | |
| 7,458,812 B2 | 12/2008 | Sporbert et al. | |
| 7,542,791 B2 * | 6/2009 | Mire et al. | 600/407 |
| 7,545,372 B2 | 6/2009 | Kopelman et al. | |
| 7,835,811 B2 * | 11/2010 | Schmitt | 700/98 |
| 2001/0002310 A1 | 5/2001 | Chishti et al. | |
| 2002/0180760 A1 * | 12/2002 | Rubbert et al. | 345/630 |
| 2003/0065259 A1 | 4/2003 | Gateno et al. | |
| 2003/0096210 A1 | 5/2003 | Rubbert et al. | |
| 2003/0215764 A1 | 11/2003 | Kopelman et al. | |
| 2004/0015176 A1 | 1/2004 | Cosman | |
| 2004/0152036 A1 | 8/2004 | Abolfathi | |
| 2004/0172150 A1 | 9/2004 | Perot et al. | |
| 2004/0185422 A1 | 9/2004 | Orth et al. | |
| 2004/0219490 A1 | 11/2004 | Gartner et al. | |
| 2004/0229185 A1 | 11/2004 | Knopp | |
| 2004/0243481 A1 | 12/2004 | Bradbury et al. | |
| 2005/0084144 A1 | 4/2005 | Feldman | |
| 2005/0089822 A1 | 4/2005 | Geng | |
| 2005/0106528 A1 | 5/2005 | Abolfathi et al. | |
| 2005/0117693 A1 | 6/2005 | Miyano | |
| 2005/0136371 A1 | 6/2005 | Abolfathi et al. | |
| 2005/0153257 A1 | 7/2005 | Durbin et al. | |
| 2005/0163342 A1 | 7/2005 | Persky | |
| 2005/0170311 A1 | 8/2005 | Tardieu et al. | |
| 2005/0214716 A1 | 9/2005 | Weber et al. | |
| 2005/0244791 A1 | 11/2005 | Davis et al. | |
| 2005/0250075 A1 | 11/2005 | Taub et al. | |
| 2005/0271996 A1 | 12/2005 | Sporbert et al. | |
| 2006/0040236 A1 | 2/2006 | Schmitt | |
| 2006/0068355 A1 | 3/2006 | Schultz | |
| 2006/0111806 A1 | 5/2006 | Kraemer et al. | |
| 2006/0263738 A1 | 11/2006 | Kuo | |
| 2007/0031791 A1 | 2/2007 | Cinader, Jr. et al. | |
| 2007/0118243 A1 | 5/2007 | Schroeder et al. | |
| 2007/0134625 A1 | 6/2007 | Leu et al. | |
| 2007/0190481 A1 | 8/2007 | Schmitt | |
| 2007/0190492 A1 | 8/2007 | Schmitt | |
| 2008/0020350 A1 | 1/2008 | Matov et al. | |
| 2008/0032257 A1 | 2/2008 | Muckler | |
| 2008/0064008 A1 | 3/2008 | Schmitt | |
| 2008/0085489 A1 | 4/2008 | Schmitt | |
| 2008/0102415 A1 | 5/2008 | Scott | |
| 2008/0228303 A1 * | 9/2008 | Schmitt | 700/98 |
| 2010/0105002 A1 | 4/2010 | Karlsson et al. | |
| 2010/0106275 A1 | 4/2010 | Andersson et al. | |
| 2011/0066267 A1 * | 3/2011 | Schmitt | 700/98 |

FOREIGN PATENT DOCUMENTS

| | | |
|---|---|---|
| WO | 2006031096 A1 | 3/2006 |
| WO | 2006096558 A2 | 9/2006 |
| WO | 2007079142 A2 | 7/2007 |

| WO | 2007084589 A2 | 7/2007 |
| WO | 2007084727 A1 | 7/2007 |
| WO | 2007130574 A1 | 11/2007 |
| WO | PCTUS07067424 | 1/2008 |
| WO | PCT07062171 | 3/2008 |
| WO | PCTUS2007062171 | 8/2008 |

OTHER PUBLICATIONS

Schmitt, The 4th Annual Eugene C. Gwaltney Manufacturing Symposium, "Rapid Prototyping and Manufacturing: Applications in Product Development, Design and Tooling", "Changing Lives with RP", Georgia Institute of Technology, Oct. 1-2, 1997 pp. 21-26 (7 pages).

Bisler, et al., "The Virtual Articulator—Applying VR Technologies to Dentistry", Proceedings of the Sixth International Conference on Information Visualisation, IEEE Computer Society, 2002 (3 pages).

Üş ümez, et al., "Inclinometer Method for Recording and Transferring Natural Head Position in Cephalometrics", American Journal of Orthodontics and Dentofacial Orthopedics, vol. 120, No. 6, Dec. 2001 pp. 664-670 (7 pages).

Kordaβ, et al., "The Virtual Articulator in Dentistry: Concept and Development", The Dental Clinics of North America, 46, 2002, pp. 493-506 (14 pages).

Murphy, et al., "The Development of Instrumentation for the Dynamic Measurement of Changing Head Posture", American Journal of Orthodontics and Dentofacial Orthopedics, vol. 99, No. 6, Jun. 1991, pp. 520-526 (7 pages).

Usumez, et al., "Effect of Complete Dentures on Dynamic Measurement of Changing Head Position: A Pilot Study", The Journal of Prosthetic Dentistry, vol. 90, No. 4, Oct. 2003, pp. 394-440 (7 pages).

Üş ümez, et al., "Reproducibility of Natural Head Position Measured with an Inclinometer", American Journal of Orthodontics and Dentofacial Orthopedics, vol. 123, No. 4, Apr. 2003, pp. 451-454 (4 pages).

Delli, "Automated Design and Fabrication of Dental Bar", University of Missouri-Rolla, Nov. 17, 2006 (23 pages).

Leu, et al., "Computer-Automated Dental Bar Design", Technology/Business Opportunity, University of Missouri-Rolla, no date (2 pages).

Gawate, "Dental Bar Design (Thesis)", University of Missouri, Published 2005 (67 pages).

Taylor, "Influence of Computerized Tomography Parameters on the Quality of Stereolithographic Models (Thesis)". The University of Texas Graduate School of Biomedical Sciences, Mar. 1999 (102 pages).

Verstreken et al. "An Image-Guided Planning System for Endosseous Oral Implants" Oct. 1998, IEEE Transactions on Medical Imaging, vol. 17, No. 5, pp. 842-852 (11 pages).

* cited by examiner

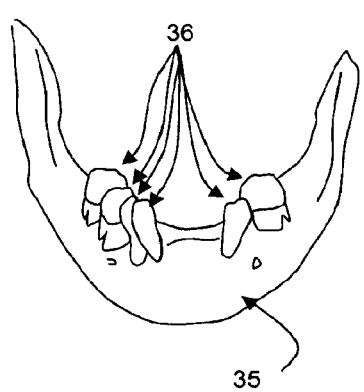 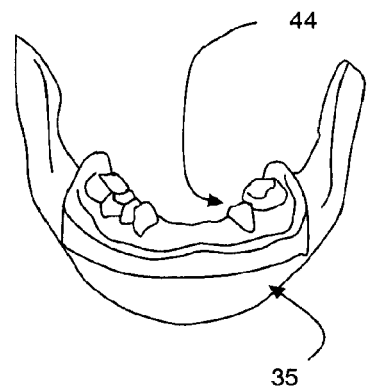 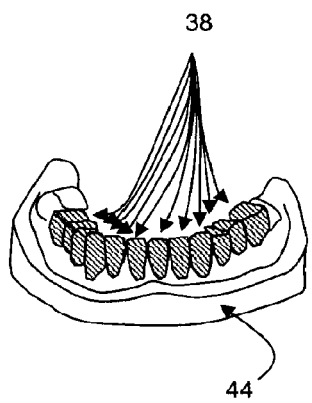
Fig. 7A    FIG. 7B    FIG. 7C
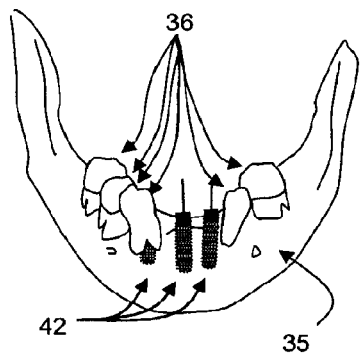
FIG. 7D

SURGICAL GUIDES AND METHODS FOR POSITIONING ARTIFICIAL TEETH AND DENTAL IMPLANTS

PRIORITY INFORMATION

This application is a divisional of U.S. patent application Ser. No. 11/867,590, filed Oct. 4, 2007, now U.S. Pat. No. 7,835,811 which claims priority to and the benefit of the filing date of U.S. Provisional Application No. 60/849,994, filed Oct. 7, 2006. The disclosure of each of the aforementioned applications is incorporated herein by reference.

FIELD OF THE INVENTION

The present disclosure is directed to methods of evaluating and treating a patient's anatomy prior to tooth removal and planning the ideal position of artificial teeth. It also is directed to methods for the computer manufacture of artificial teeth attached to dental implants.

BACKGROUND OF THE INVENTION

Patient preparation and implantation of dental implants may be accomplished in different ways. For example, one method uses a radiographic template made to fit to the patient's teeth. Radiographic markers are attached to this template. Another method, disclosed in U.S. Pat. No. 5,967,777 to Klein, uses a plastic replica of the prospective teeth to be supported by dental implants. This is a time consuming process since a dental laboratory technician must set or carve teeth to fit in the ideal position for a given patient. The patient is then scanned with the radiographic template, preferably using computed tomography (CT). If the patient has teeth that will be removed at the time of implant placement it is difficult to image these areas since the teeth are still present and frequently radiographic scatter makes it difficult to determine the actual shape of the teeth. It is also difficult to position the template in a predictable position after the teeth are removed. Yet other methods have been revealed that require the patient's teeth to be removed first and removable dentures made. The NobelGuide™ (Nobel Biocare) system uses this technique. After healing, radiographic markers are placed in the dentures and the patient is imaged using CT. A second scan of the patient's denture is made of the denture alone and then the radiographic markers are used to align the two CT scans in the same computer space. This system allows for planning of the dental implant position in relation to the patient's denture and the supporting bone but it does not allow for planning the shape of the bone if reshaping is needed to have adequate space for restorative materials or to have the proper ridge form for the dental implant. It also requires the patient to wear removable dentures and many patients would prefer to have their teeth removed, implants placed and artificial teeth attached to the implants all during one surgical procedure. This system also does not allow for changes in the position of the artificial teeth after the denture has been imaged.

Thus, there is a need for an improved method of imaging a patient and planning for implant placement that provides for the virtual extraction of teeth to determine the shape of remaining bone, virtual positioning of artificial teeth that are in harmony with the patient, virtual shaping the remaining bone to provide proper space and form for restorative materials, and virtual positioning implants in relation to the remaining bone. There is also a need for a method of communicating this information easily to the surgeon, restorative dentist and laboratory. It is also desirable that changes can be made in the virtual plan such that the surgeon, restorative dentist or laboratory can modify the treatment plan as needed. Furthermore, it is desirable that surgical templates and artificial teeth be manufactured using computer technology to insure precise and predictable results with minimal manual labor. Finally, there is a need that the process allows for the creation of surgical guides, artificial immediate dentures and immediate load prosthesis prior to surgery and with a system that allows for precise orientation of the immediate load prosthesis at the time of tooth removal and implant placement.

The systems and methods of this disclosure address one or more of the shortcomings in the prior art.

SUMMARY OF THE INVENTION

The present invention relates to a method of evaluating a patient's anatomy prior to tooth removal and planning the ideal position of artificial teeth, creating surgical templates to shape bone and a method of drilling and installing dental implants. The present invention also provides for the computer manufacture of artificial teeth attached to dental implants at the time of surgery and to shape the teeth to be in harmony with opposing teeth and the patient's jaw movement.

U.S. patent application Ser. No. 11/674,956, titled Method for Making a Virtual Computer Model of the Jaws, filed Feb. 14, 2007, incorporated herein in its entirety by reference, reveals a method of using computed tomography (CT) to image the hard and soft tissues of the head and neck. It also reveals a method of imaging dental casts of a patient using non-radiographic techniques to eliminate radiographic scatter caused by dental restorations in CT scans.

U.S. patent application Ser. No. 11/739,310, titled Computer Machined Dental Tooth System and Method, filed Apr. 24, 2007, incorporated herein in its entirety by reference, reveals a method of tracking the positional relationship of the upper and lower jaw with static records (wax bites) average measurements and a digital recording device called ARCUSdigma digital recorder (KAVO Company). It also reveals a method of virtually positioning artificial denture teeth and using computer milling to shape the teeth and the dental cast to construct immediate dentures using digital technology.

U.S. patent application Ser. No. 11/851,105, titled Methods for the Virtual Design and Computer Manufacture of Intra Oral Devices, filed Sep. 6, 2007, incorporated herein in its entirety by reference, reveals a method of imaging dental casts, recording spatial relationships and creating virtual movement of the models such that actual devices can be made with computer technology. The methods revealed in these applications are used as the basis for creating the virtual models used in this invention.

In some embodiments, the exemplary methods and systems disclosed herein create a virtual computer model of a patient's mouth and to ideally position virtual artificial teeth in proper spatial orientation to the supporting tissues, teeth and the opposing arch. The positioning of teeth is determined by the use of virtual planes, curved surfaces or other digital references rather than the mechanical devices used in prior art.

In some embodiments, the exemplary methods and systems disclosed herein provide a method to virtually remove the patient's teeth from the virtual model of the supporting bone to determine the ideal position to place implants after the teeth have clinically been removed.

In some embodiments, the exemplary methods and systems disclosed herein provide a method for the surgeon and restorative dentist to virtually reshape bone to provide adequate space for restorative materials and to create an ideal osseous form for implant placement.

In some embodiments, the exemplary methods and systems disclosed herein provide a method for the restorative dentist, surgeon and laboratory to communicate and change if needed, the actual 3D virtual plan for any given patient via the Internet.

In some embodiments, the exemplary methods and systems disclosed herein use advanced computer manufacturing techniques (milling and layered manufacturing) to make drill guides, immediate dentures and immediate load prosthesis with minimal manual labor.

In some embodiments, the exemplary methods and systems disclosed herein provide a novel dental implant placement method to ideally position dental implants in supporting bone and to record the positional relationship of the dental implants in relation to the opposing arch for the connection of the immediate load prosthesis to dental implants.

Finally, in some embodiments, the exemplary methods and systems disclosed herein provide a method of evaluating the aesthetic appearance of a patient prior to tooth removal and to use virtual techniques that allow for the selection of ideal replacement teeth, shaping the supporting bone, placing implants, construction of surgical guides and immediate prosthesis all via the Internet such that many individuals in different parts of the world can communicate and support the process of planning and treating patients that require implant therapy.

In one exemplary aspect, the present disclosure is directed to a method of creating a surgical drill guide. The method includes the steps of generating a virtual model of a portion of a patient's jaw and introducing virtual dental implants to the virtual model. It also includes generating a virtual drill guide shaped to fit on the virtual jaw, the virtual drill guide indicating the position of the virtual dental implants, and manufacturing an actual drill guide based on data of the virtual drill guide.

In yet another exemplary aspect, this disclosure is directed to a method of aligning a patient's bite position. The method may comprise generating a virtual model of an upper jaw with upper teeth and a lower jaw with lower teeth of a patient; creating a virtual index between the upper teeth and the lower teeth, the virtual index having indentations shaped to fit the upper teeth and lower teeth of the patient, and indicating a bite position of the lower jaw relative to the upper jaw of the virtual model; manufacturing an actual index based on data of the virtual index; arranging the actual index in place on at least one tooth of the actual upper or lower teeth in the patient's mouth; affixing impression copings to the actual index, the impression copings identifying positions of in-place dental implants; and tracking a bite position of the actual lower jaw relative to the upper jaw using the impression copings and the actual index.

In another exemplary aspect, the present disclosure is directed to a method of implanting dental implants. The method comprises removing at least one first tooth from a patient's jaw; placing a first surgical drill guide in the patient's mouth, the first surgical drill guide being oriented relative to at least one second tooth in the patient's jaw; drilling a bore in the patient's jaw using the first surgical drill guide; removing the at least one second tooth from the patient's jaw; inserting a guide pin in the bore; placing a second surgical drill guide in the patient's mouth, the second surgical drill guide being oriented relative to the guide pin in the bore; and implanting a dental implant based on the position of the second surgical drill guide.

In another exemplary aspect, the present disclosure is directed to a method of aligning a patient's bite position. The method may include inserting at least one first dental implant in a patient's mouth; orienting a first impression coping on the first dental implant; arranging an occlusal index in place on at least one tooth of actual upper or lower teeth in the patient's mouth; affixing the first impression coping to the occlusal index, the impression coping identifying the relative position of the at least one first dental implant; removing the actual index and the affixed first impression coping from the mouth; inserting at least on second dental implant in the patient's mouth; orienting a second impression coping on the at least one second dental implant; orienting a third impression coping on the at least one first dental implant; and rigidly connecting the second and third impression copings to identify the position of the second dental implant relative to the first dental implant.

BRIEF DESCRIPTION OF THE DRAWINGS

FIGS. 7A-7D are illustrations of a virtual model of the lower jaw, respectively showing teeth, dental cast in place on the lower jaw, artificial teeth positioned in space, and dental implants with the teeth removed.

DETAILED DESCRIPTION

Figure 1:
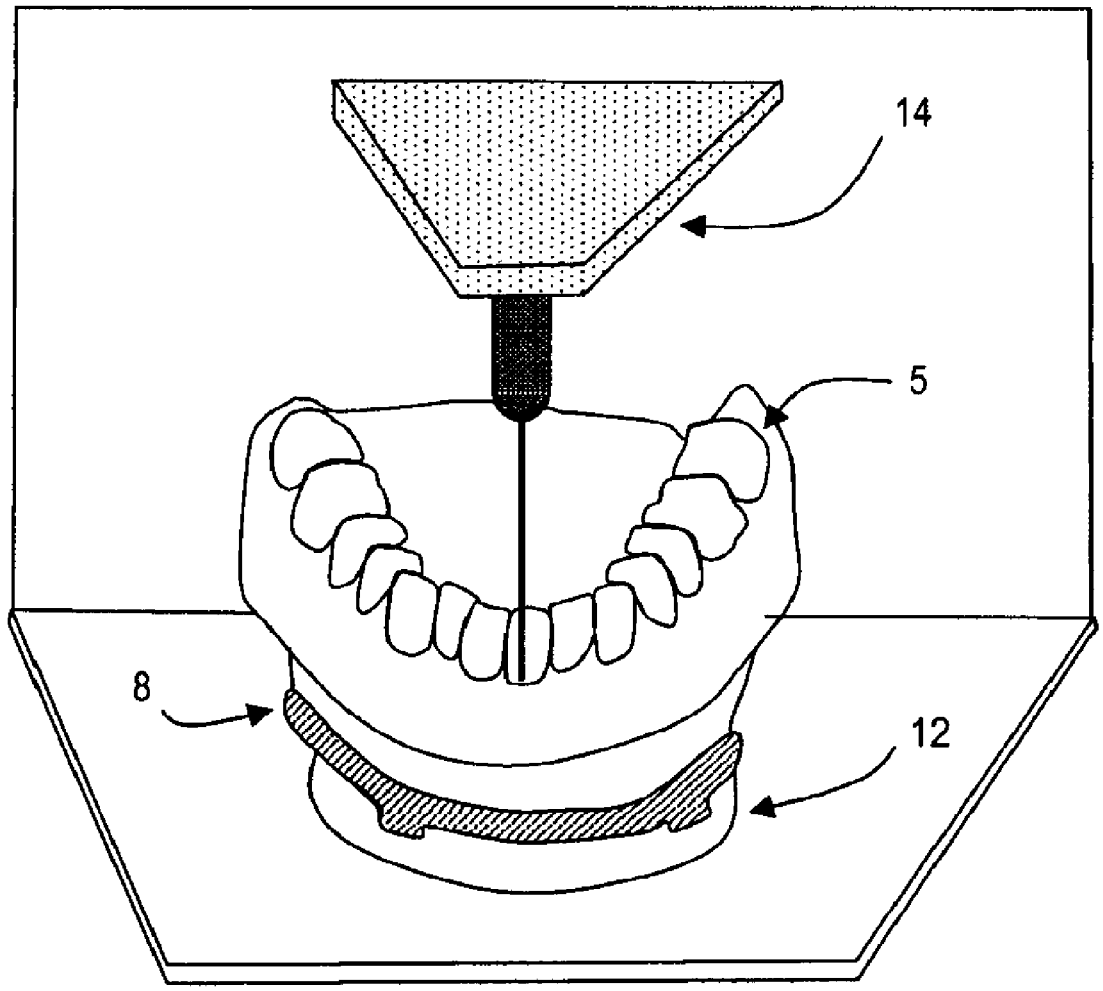
FIG. 1 is a schematic view of the lower cast attached to a reference plate in a digital 3D scanner.

For the purposes of promoting an understanding of the principles of the invention, reference will now be made to embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 illustrates a lower cast 5 joined to a mounting plate 8 seated in a mounting plate receiver 12. The cast 5 is positioned in a digital imaging system 14 and can be imaged with contact, light, laser, radiographic, or holographic imaging techniques. The imaging system creates a data set of the 3D surface of the dental cast 5 in a known spatial relationship to the mounting plate receiver 12. The data can be stored in computer memory as a text file recording specific x, y and z points in relation to the mounting plate receiver or the points can be altered to produce a mathematical surface or solid model of the dental cast using mathematical algorithms known in the imaging art. A preferred method is to save the surface of the dental cast as a .stl (stereolithography) file which records the surface as a series of small triangles. The upper dental cast (not shown in FIG. 1) is imaged in the same manner to create a data set for the surface of the upper cast in relation to the mounting plate receiver.

Figure 2:
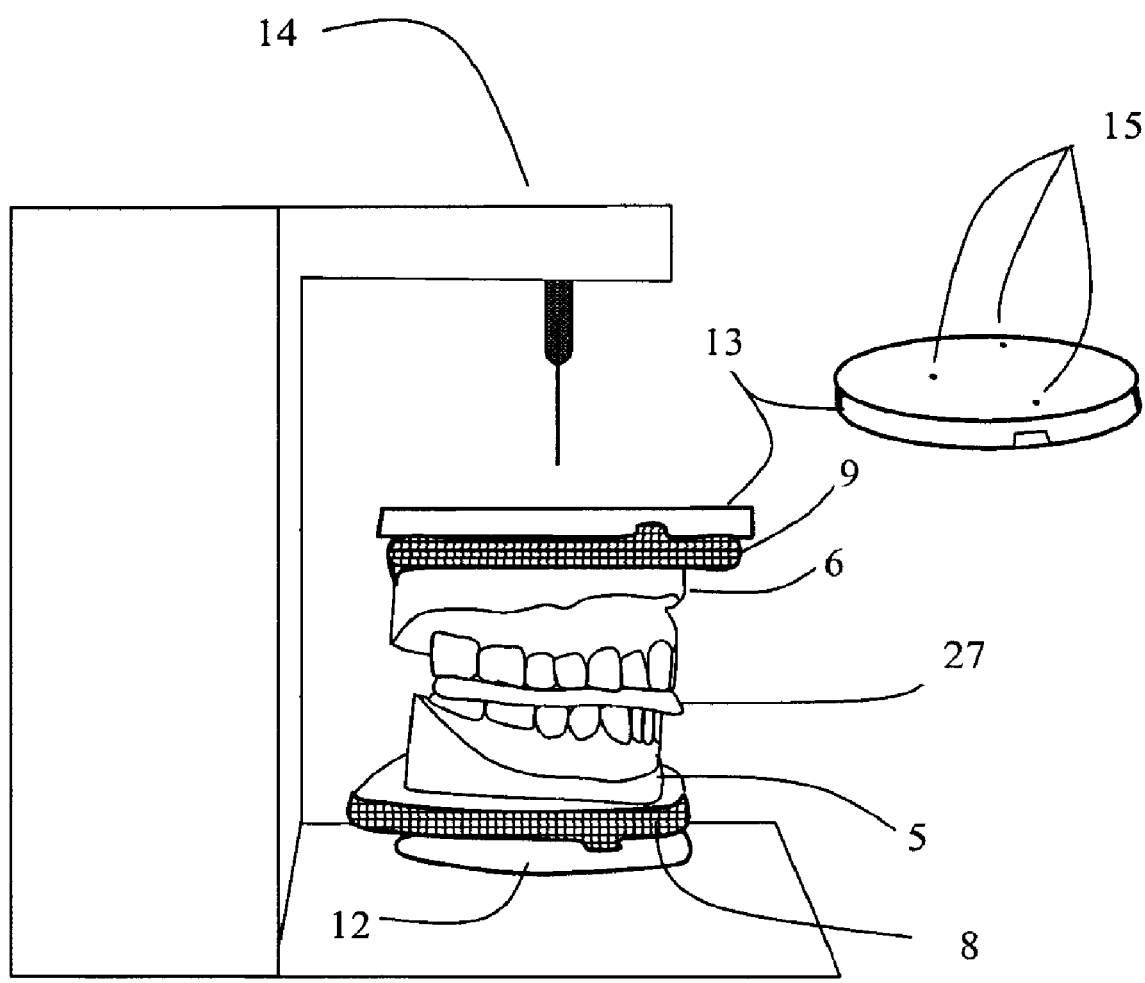
FIG. 2 is an illustration of an exemplary system for determining the positional relationship of the upper cast to the reference plate on the scanner with a wax bite record.

Turning now to FIG. 2 of the drawings, there is depicted the upper cast 6 and lower cast 5 on an imaging system, such as a digital scanner 14. The lower cast 5 is seated in the mounting plate receiver 12 and the upper cast 6 is held in position with a wax bite record 27. The bite record 27 was made by a dentist and records the orientation of the upper teeth to the lower teeth so that the casts 5, 6 can reproduce the same orientation and relative position as the patient's actual teeth. A calibrating mounting plate receiver 13 is attached to the upper mounting plate 9. In FIG. 2, the calibration mounting plate receiver 13 is shown both on and off the cast 6. The calibrating mounting plate receiver 13 is used to record the spatial orientation of the upper mounting plate 9 to the scanner 14 and its mounting plate receiver 12. The calibrating mounting plate receiver 13 has three small indentations 15 on its upper surface that can be detected with the scanner 14 and may be used to move upper cast scan data in computer space using a three-point move (Cadkey® Baystate Technologies Inc.). This allows a user to position scan data relating to the upper cast 6 and bite record 27 in the same orientation in a virtual model as exists in the patient's mouth.

Figure 3:
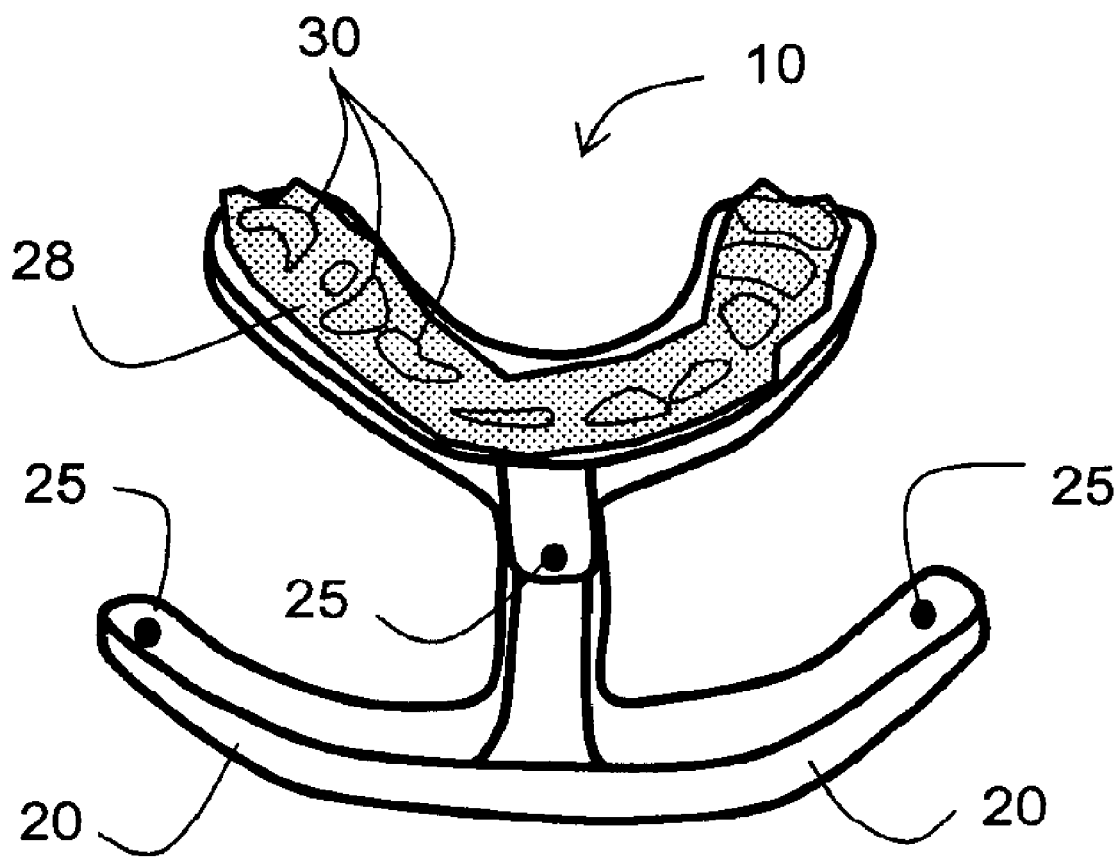
FIG. 3 is an illustration of an exemplary CT bite plate.

Referring to FIG. 3, there illustrates an exemplary CT bite plate assembly 10. The bite plate assembly 10 has a U-shaped rigid section attached to a thin bite surface made of a radiolucent material that is configured to mate with the patient's teeth and yet have minimal opening of the jaws. The bite surface has a central forward projection that extends between the lips when the assembly is placed in the mouth. The forward projection is joined to a vertical portion that extends above or below the plane of occlusion. Wings 20 extend laterally from the vertical portion and follow the contour of the face but do not contact it. Three or more non-linear radiographic markers 25 are attached to the vertical and wing portions of the CT bite plate. These markers 25 have a radiographic density that makes them visible in the CT data and also have a geometric shape that can be imaged with contact, light, laser, or holographic imaging techniques. Bite registration material 28 records the indentations 30 of the upper and lower teeth when the patient bites into the CT bite plate 10.

Figure 4:
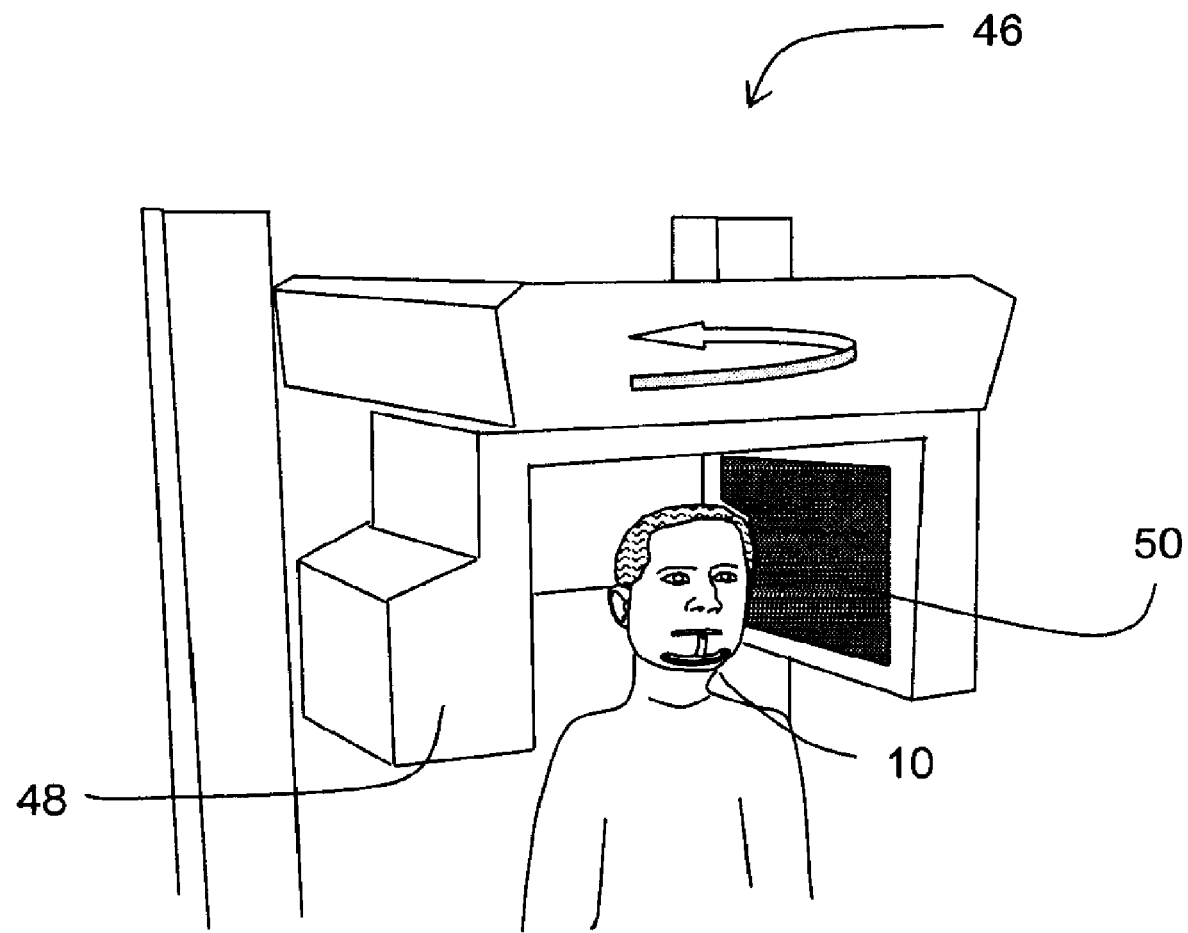
FIG. 4 is an illustration of the CT bite plate in the patient's mouth during the CT scan.

FIG. 4 illustrates the CT bite plate assembly 10 placed in a patient's mouth and the patient positioned in a CT machine 46. An x-ray source 48 projects radiation across the patient's head and is detected on a sensor 50. As disclosed further below, using the data obtained from this CT scan, an image of the patient's jaws and teeth may be generated.

Figure 5:
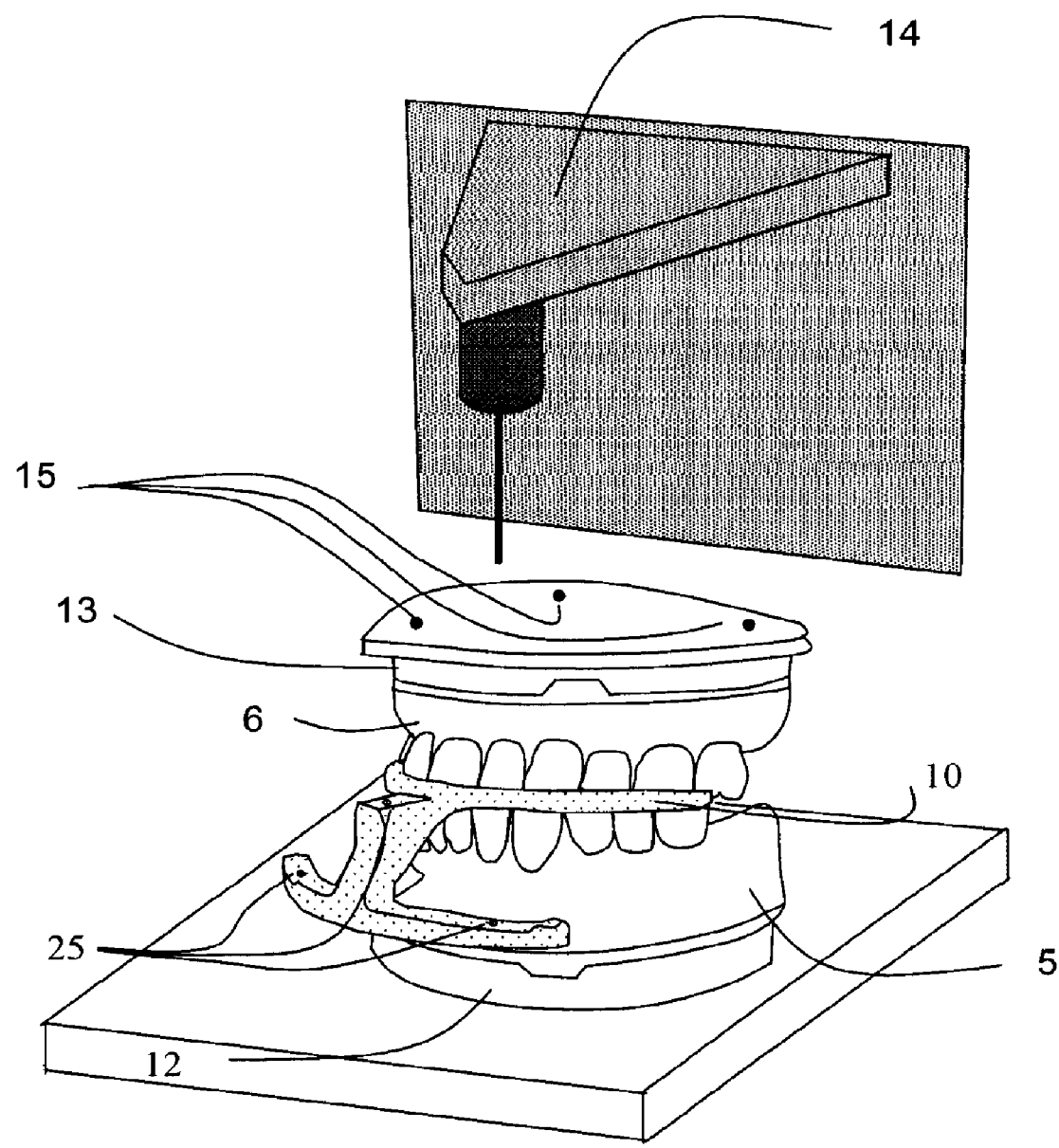
FIG. 5 is an illustration of an exemplary preferred embodiment for determining a positional relationship of an upper cast to a reference plate on a scanner with the CT bite plate.

FIG. 5 illustrates the CT bite plate assembly 10 removed from the patient's mouth and attached to the upper dental cast 6 and the lower dental cast 5 on an imaging system, such as the digital scanner 14. Because of the bite registration material 28 in FIG. 3, the teeth of the upper and lower dental casts 5, 6 can have a relative position that nearly identically matches that of the actual teeth recorded in the CT scan in FIG. 4. Once scanned, in virtual computer space, the position of the three radiographic markers 25 can be located and the location of the three indentations 15 on the calibration mounting plate receiver 13 can be used to move and record the orientation of virtual images of upper cast 6 in relation to images of the lower cast 5. Data from the CT scan may be saved as two dimensional grayscale bitmaps (DICOM format) and can be processed with volume rendering software to create 3D data sets of objects with specific grayscale values. Each object can then be saved as a 3D object in a known position in computer space. Since the dental casts 5, 6 were scanned in computer space in an orientation different than the patient CT scan, the image data representing the three radiographic markers on the CT bite plate assembly 10 are used to move the orientation of the cast image data to the same position as the CT data using a 3-point move in the CAD software. Many file formats are available to save the three dimensional shape of a give object. The preferred embodiment is the .stl (stereolithography) file. This is an efficient format that saves the surface of the object as small triangles in a known computer space.

Figure 6:
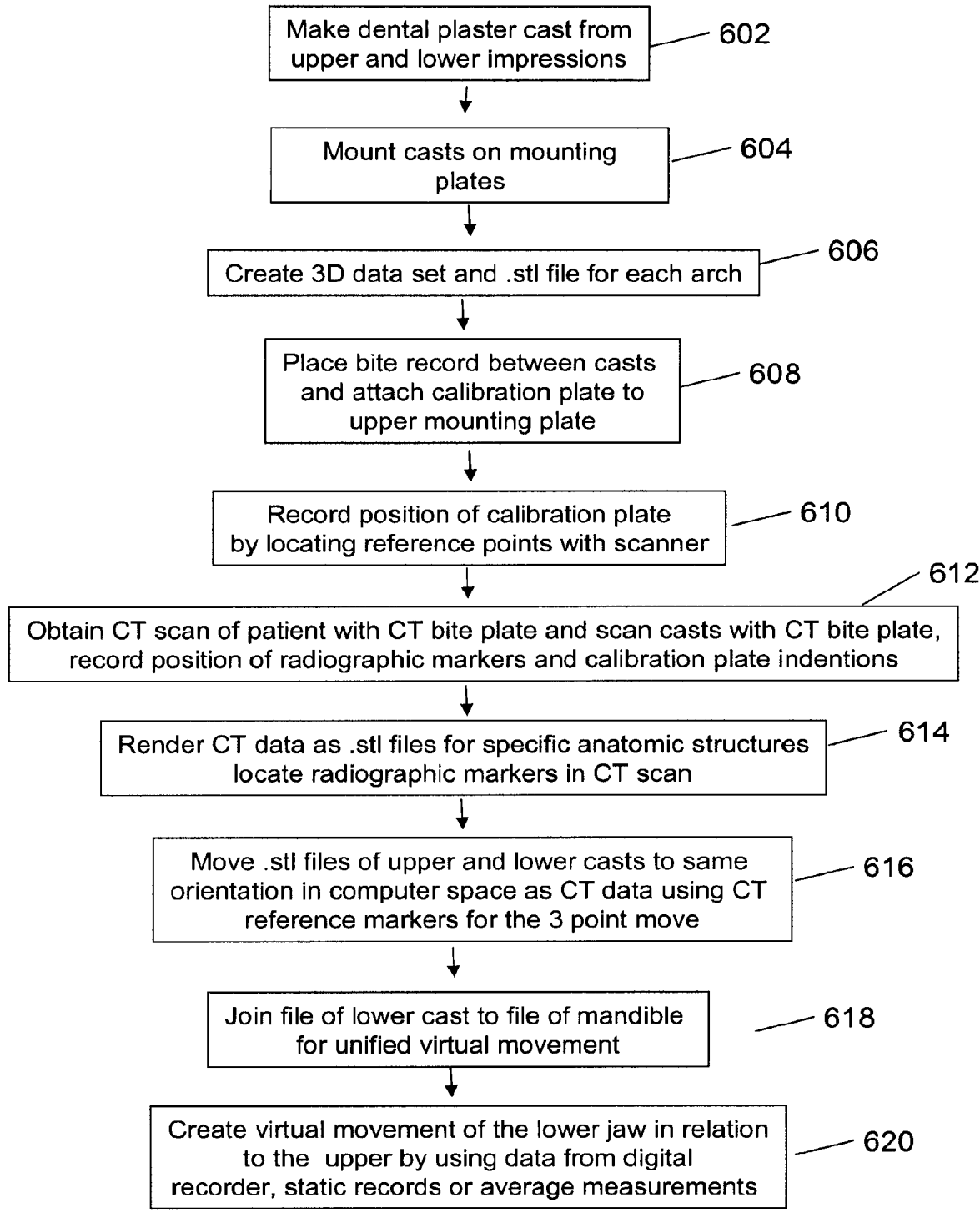
FIG. 6 is a flow chart showing an exemplary process of making a virtual model of the patient.

FIG. 6 illustrates an exemplary process of scanning the dental cast models 5, 6 and joining the scan data of the dental cast models to the CT data of the patient scan in the same spatial relationship. Portions of this process are disclosed in previously filed U.S. application Ser. No. 11/674,956, titled Method for Making a Virtual Computer Model of the Jaws, filed Feb. 14, 2007.

As shown in FIG. 6, this process begins with a dental care provider, such as a dentist, technician, or other provider making a dental cast from upper and lower impressions as indicated at step 602. Once made, the provider mounts the casts on mounting plates as indicated at step 604 and creates a 3D data set and .stl file for each of the upper arch and the lower arch at step 606. This is explained above with reference to FIG. 1.

A bite record may be placed between the casts and a calibration plate may be attached to one of the upper and lower mounting plates at step 608. At step 610, the position of the calibration plate is recorded by locating reference points with scanner. As discussed above with reference to FIG. 2, the reference points may be indentations in the mounting plate or other reference points.

At step 612, a CT scan of the patient is taken, as shown in and discussed relative to FIG. 4. The CT scan records data of the patient's actual anatomical structure in order to render a 3D image. In addition, at step 612, the dental casts are scanned with the CT bite plate in order to render a 3D image. The provider also may record the position of radiographic markers. One example of a CT bite plate is described with reference to FIG. 3 and shown between exemplary upper and lower casts in FIG. 5. The CT bite plate includes at least three radiographic markers that, when scanned and reproduced as a virtual image, may be used to align the casts in computer space to have substantially the same orientation and relative position as the patient's actual teeth.

At a step 614, CT data is rendered as .stl files for specific anatomic structures and for casts and the radiographic markers are located in the CT scan. At step 616, the provider manipulates the 3D files of the upper and lower casts so that they have the same orientation in computer space as the CT data of the patient's anatomical structure. This is done by aligning the markers on the CT bite plate in the scan of the upper and lower casts with the markers on the CT bite plate of the CT scan of the patient. Aligning the three CT reference markers in computer space so that the scanned casts have nearly the exact position of the patient's teeth may be referred to as a 3-point move. It should be noted aligning the scans of the casts into the same position as the CT data allows viewing of the plaster cast teeth in relation to the remaining bone and roots. Doing This also eliminates the radiographic scatter that may have occurred when the patient was scanned using CT, and replaces the scatter with images of the casts. Thus, the image is cleaner and provides more precision than if only the CT scan of the patient were used.

At step 618, the 3D file of the lower dental cast is joined to the 3D file of the mandible of the patient for unified movement in computer space. At step 620, virtual movement of the lower jaw relative to the upper jaw may be created using data from a digital recorder, static records, or average measurement. This data may have been obtained, such as when using the digital recorder, by scanning the patient's jaws while he or she moves the upper and lower jaws relative to each other, thereby tracking the pathway of relative movement. These recorders may include ultrasound, infrared, light and other methods of recording the positional relationships. The ARCUSdigma (KaVo Company) digital recorder may be ideally suited for this task. The movement data also may have been obtained by taking multiple static records of the patient's jaws in different positions relative to each other. The compilation of such static records may be used to create a pathway of jaw movement, allowing the provider to track the pathway of movement. In some embodiments, the pathways of movement may be determined by calculations based on size measurements and other data for the patient himself or for average data taken from a number of patients. These recorded, determined, and calculated pathways of movement are referred to herein as pre-determined paths of movement.

While some exemplary versions of the processes described above for obtaining 3D renderings include taking a CT scan of the patient, in other exemplary versions, only the casts are scanned. Therefore, the images of the casts are not placed with or aligned with an image of the patient. As described above, in some examples, these casts still may be oriented with a bite record allowing the 3D rendering of the top and bottom casts to be oriented relative to each other in the manner similar to the relative orientation of the patient's actual teeth.

Once the data is stored as a computer data file, the data can be used to create surgical drill guides and indexing components that assist in the location of dental implants, denture teeth, dentures, and immediate load prostheses.

Many methods have been developed to create surgical drill guides for implant placement. The vast majority of drill guides are manufactured on a dental cast. The dental cast is an ideal medium for this process since it is possibly the most accurate reproduction of the patient's anatomy and the cast can be easily scanned to create a precise digital image. The cast is also useful since many laboratory procedures use the cast to process or manufacture the drill guide or the actual artificial teeth or other devices. Some examples are the "salt and pepper" method of adding auto-polymerizing resin to a cast or the process of "heat processing" dentures. The cast is also a better representation of the patient since the impression technique used to make the cast can displace soft tissues to record unique anatomic structures such as the hamular notch, retro-molar pad or muscle attachments using border molding techniques. Grayscale data from CT scans do not reproduce these structures accurately. One known prior reference (European Patent 0756735 Simplant) discloses using grayscale data from CT to create a medical model of the human body and to modify it by adding additional functional elements. There are many problems with this process. The accuracy of the surface of the teeth from CT is much less than the accuracy of the surface created using impression techniques. Also, radiographic scatter from metal crowns and fillings may make the teeth impossible to record. This reference also uses rapid prototyping to produce the actual drill guide. Present rapid prototyping processes are improving but the accuracy and selection of materials to use with the process are not as vast as those available for conventional laboratory processes or for number controlled milling. In order to overcome some of the limitations of the prior art, in a preferred embodiment of this disclosure, scan data from the dental cast is used to design and create the drill guide and replacement teeth. By using this data, precise and accurate devices can be made from a vast array of materials and conventional dental processing techniques can also be used.

FIG. 7A illustrates one example of a virtual model of a virtual lower jaw 35 and virtual teeth 36 from CT data as it may appear on a computer display. The teeth 36 and roots may have a different radiographic density than the bone of the lower jaw 35, allowing a user operator to identify them by their gray-scale value relative to the gray-scale value of the lower jaw. As indicated above, this virtual model may include information from the CT scan of the patient, as well as information from the CT or other scan data from the dental plaster casts. FIG. 7B illustrates the virtual lower jaw 35 and the virtual lower cast 44 positioned in the same spatial orientation in computer space. This may be done by replacing the surfaces of the virtual model with that of the virtual image of the plaster cast. Once the virtual images of the patient's actual teeth are removed from the virtual model, virtual denture teeth may be added to the virtual model. FIG. 7C shows virtual denture teeth 38 positioned in one exemplary ideal relationship relative to the virtual lower cast 44 and opposing teeth (not shown). To do this, these virtual denture teeth 38 may be individually stored as .stl files or other computer files, and may be imported and added to the virtual model of the dental cast 44 using Boolean operations. Alternatively, these virtual denture teeth 38 may be stored in sets or groups that are added to the virtual model of the dental cast 44. In some exemplary embodiments, the virtual denture teeth files are created by scanning actual denture teeth and storing the resulting data. FIG. 7D illustrates the virtual jaw 35 with virtual teeth and roots from the CT scan 36 and the virtual anterior implants 42 placed to provide ideal boney support in the virtual plan. In FIG. 7D, the lower shaded elements of the implants 42 are imbedded within the boney support of the virtual jaws.

In some embodiments, rather than removing virtual teeth and adding virtual denture teeth, these processes are performed on actual casts. For example, the actual denture teeth may be placed on the actual cast of the jaw. This cast with the placed teeth may be converted to digital data using a scanning or other process and may include a portion of the steps of FIG. 6.

Note that any of the images discussed herein may be stored as 3D virtual models and sent via the Internet or other network to other clinicians or the patient for review or modification using suitable software. In one example, suitable software may include FREEFORM™ (SensAble Technologies Inc.).

Figure 8A:
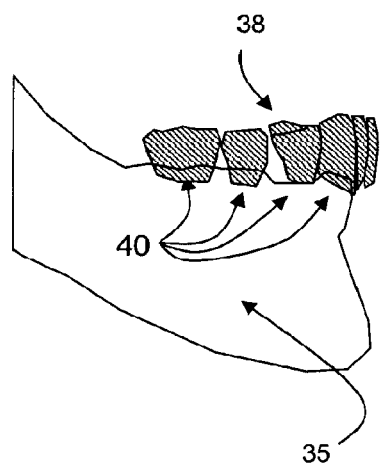
FIG. 8A shows virtual artificial teeth positioned relative to the virtual lower jaw.

FIG. 8A is another view of the virtual denture teeth 38 positioned relative to the virtual lower jaw 35, as in FIG. 7C. With the virtual teeth placed in a desired position, there may be areas, indicated by the reference numeral 40, where the denture teeth 38 and the bone of the lower jaw 35 overlap or interfere. In these areas, and also potentially in some areas where the virtual teeth and bone do not overlap, there may be insufficient space for restorative materials that secure the denture teeth to the bone. Some examples of restorative materials that may be hygienic and/or strong and may include gold, titanium, porcelain, or acrylic resin, among others.

Figure 8B:
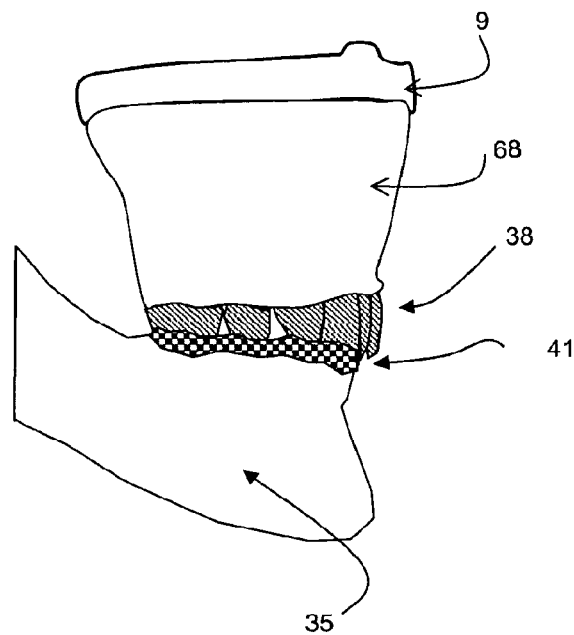
FIG. 8B shows the required restorative space and virtual stone index.
Figure 8C:
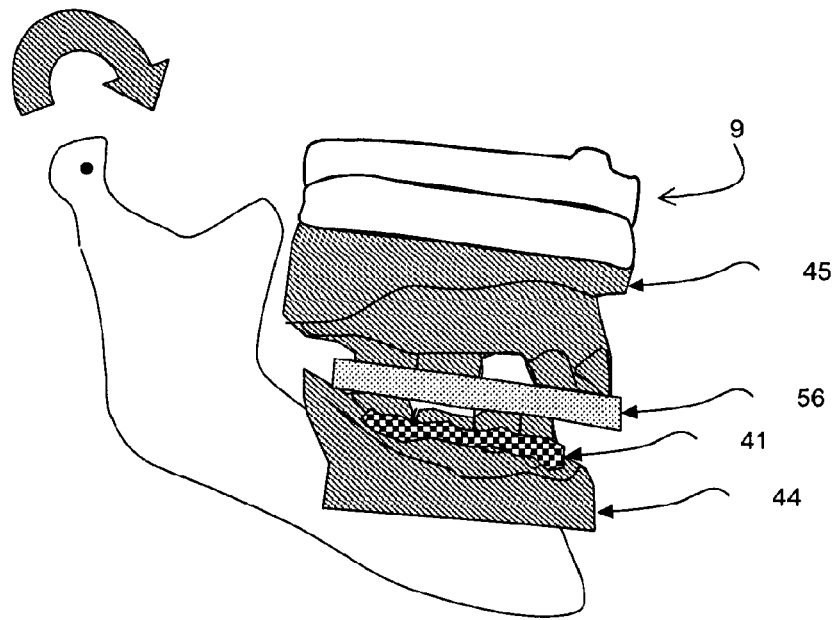
FIG. 8C shows the upper and lower virtual cast and virtual occlusal index.
Figure 13:
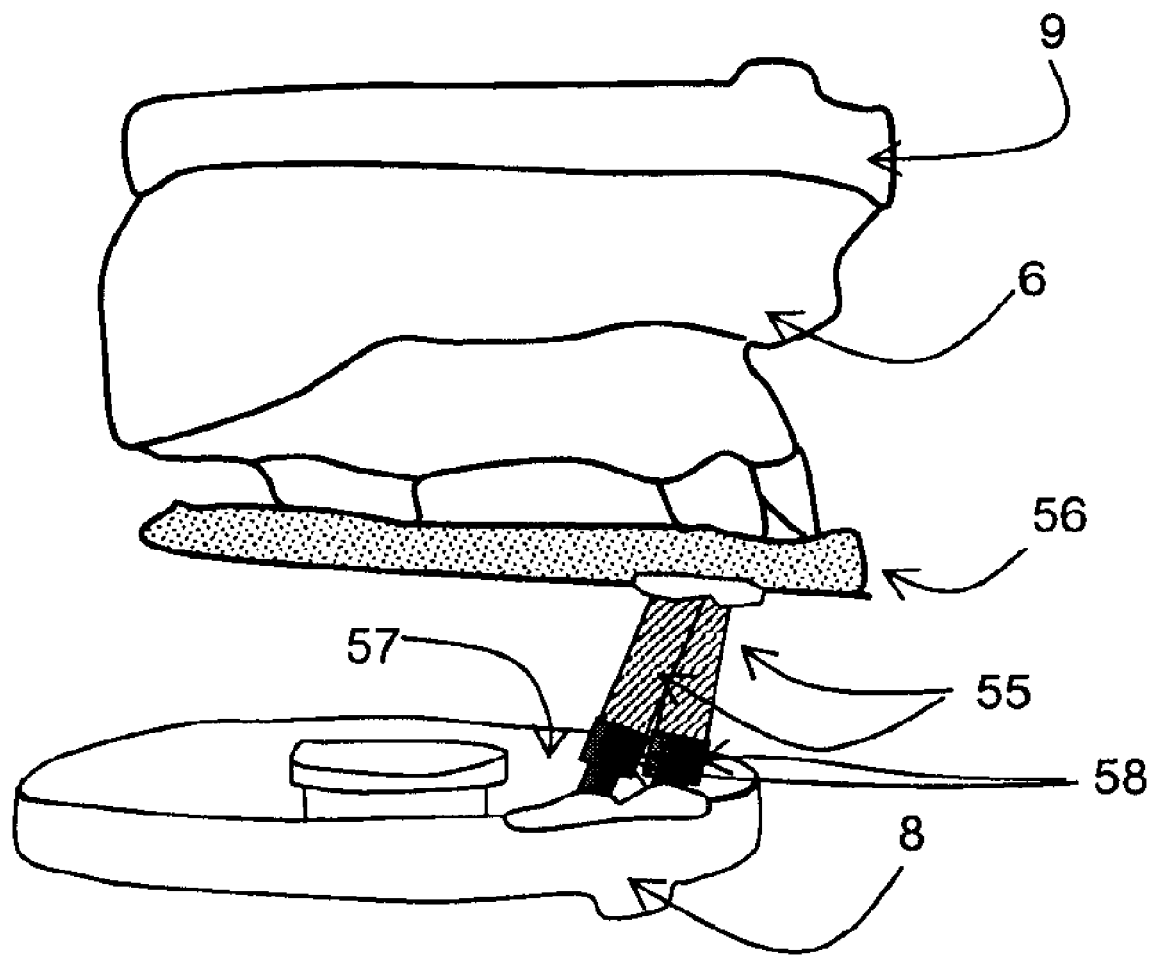
FIG. 13 is an illustration of laboratory analogues positioned into impression copings and luted to a lower mounting plate.
Figure 16:
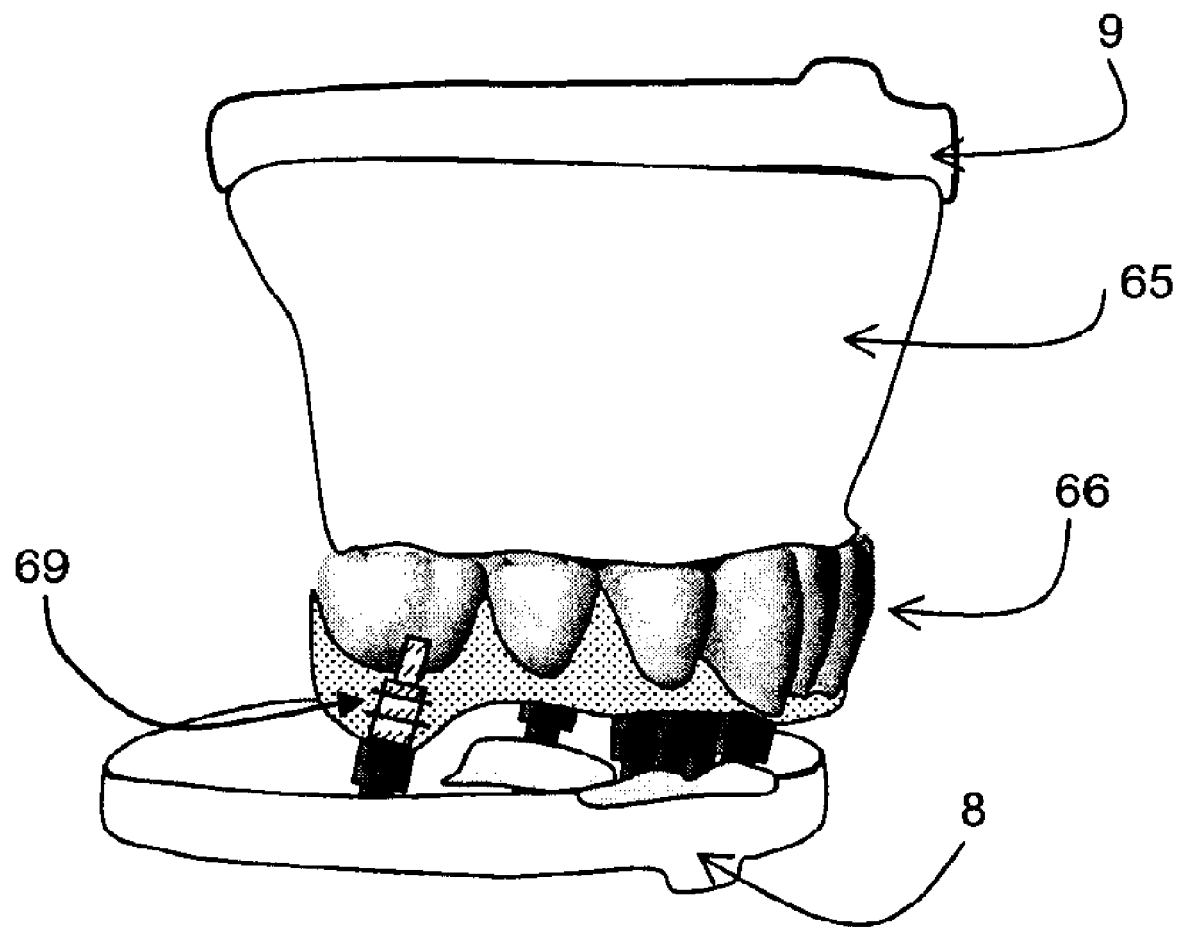
FIG. 16 is a drawing of a lower immediate load prosthesis attached to an upper stone index and temporary cylinders being joined to the prosthesis.

In order to provide the desired spacing between the patient's lower jaw and denture teeth, portions of the jaw bone may need to be removed at the time for surgery. FIG. 8B illustrates a virtual image of the virtual lower jaw 35 and virtual denture teeth 38. Area 41 indicates the area that the denture teeth and the bone overlap and the space that must be created in order to secure the actual artificial teeth. This space is called "restorative space" in the dental art and indicates the amount of space required to have a restoration that is strong, hygienic and esthetic. Area 41 between the virtual jaw 35 and virtual denture teeth 38 can be increased, reduced, or otherwise modified with computer software such as, for example, FREEFORM™ (SensAble Technologies Inc.) to view and change the shape of the virtual jaw 35, virtual lower cast, or virtual denture teeth 38 using tools similar to objects in the real world. Also illustrated in FIG. 8B is a virtual stone index 68. This index 68 is sized to fit the lower teeth when they are in position as though the jaws are more open or in a more separated position than will result when new teeth are placed at the time of surgery. This open jaw position provides space for an occlusal index 56 illustrated in FIG. 8C. This same precise open jaw position is illustrated in FIG. 8C, FIG. 13, and FIG. 16. By knowing the spatial orientation of the mounting plates 9 and 8 in the virtual model, the same orientation can be recreated with real devices in the lab. FIG. 8C shows the virtual upper cast 45 virtual lower cast 44 and occlusal index 56 with the jaw opened the same amount as in FIG. 8B. The amount of restorative space needed at the time of surgery is indicated 41. Using Boolean operations the virtual dental cast 45 and 44 can be cut from the virtual occlusal index 56. This 3D data set of the index can be translated into number controlled milling code to cut a piece of methylmethacrylate or similar material into a form identical to the virtual one. Finally, the space indicated for restorative materials 41 can also be used to modify the lower virtual cast and be translated into number controlled milling code to mill the actual lower dental cast identical to the virtual one.

As described below, suitable locations of dental implants 42 and the denture teeth 38 may be determined using one or more of an occlusal index, a first drill guide, and a second drill guide. The occlusal index may be based upon scan data and may have formed indentations that fit precisely to both the upper teeth and the lower teeth at a position suitable for the patient's bite. This index may record the locational relationship of the dental implants to the patient's teeth and may be used to transfer that locational relationship to the casts that have been mounted on the mounting plates. As explained below, it also may allow for the precise orientation of an immediate load prosthesis and may allow for joining of the prosthesis to temporary cylinders using laboratory processes outside the mouth.

In some embodiments, the occlusal index may be computer milled from a material, such as, for example, methylmethacrylate resin to fit to both the upper cast and the lower cast using scan data from the dental casts. The index also may record an exemplary ideal jaw relationship for the patient's prosthesis, possibly eliminating the need for guiding the patient into any specific jaw position during surgery and possibly eliminating the need for using soft tissue to index the correct position for the immediate load prosthesis.

The first and second drill guides may identify suitable drilling positions, with desired angles and depths in the patient's mouth. As described below, the first drill guide may be placed within the patient's mouth relative to some of the patient's actual teeth. The second drill guide may be placed within the patient's mouth after all the patient's teeth are removed. In this case the second drill guide is placed relative to a hole drilled while using the first drill guide.

Once the virtual jaw bone is modified as described above with respect to FIGS. 7 and 8, the virtual teeth 36 may be restored in their prior position relative to the jaw. Alternatively, only some of the teeth and a portion of the jaw bone may have been removed and modified. In order to precisely reshape the remaining bone and to ideally place the dental implants, the virtual teeth 36 may be removed in a sequential manner. For example, some teeth may be removed to allow for reshaping the bone and placement of two or more implants, as shown in FIGS. 10 & 11. However, in a preferred method at least three other teeth remain to provide a tripod effect that will be used to position the first surgical drill guide. As further explained below, once the first two dental implants are rigidly secured in the bone, impression copings may be attached to the two dental implants and the copings may be joined to the computer generated occlusal index to record the position of the implants in relation to the remaining lower teeth and also in relation to the upper teeth.

This process differs from known conventional immediate load systems. For example, the DIEM™ system (Implant Innovations, Inc) uses soft tissue (the vestibule and retromolar pads) to position the surgical guide in the mouth. This is a very unpredictable process since the tissue can move and the patient is frequently sedated so that it is difficult to determine the correct location of the guide. The DIEM™ system also has the disadvantage of attaching the immediate load prosthesis in the mouth with acrylic resin. A thin sheet of rubber is placed between the bone and the prosthesis to prevent the acrylic resin from flowing into the wound. This is also unpredictable and time consuming since the surgeon must wait while the acrylic resin cures in the mouth and has to be sure the resin does not burn the patient as it cures. It is also difficult to be sure the provisional prosthesis is in the correct orientation to the opposing teeth.

Figure 9:
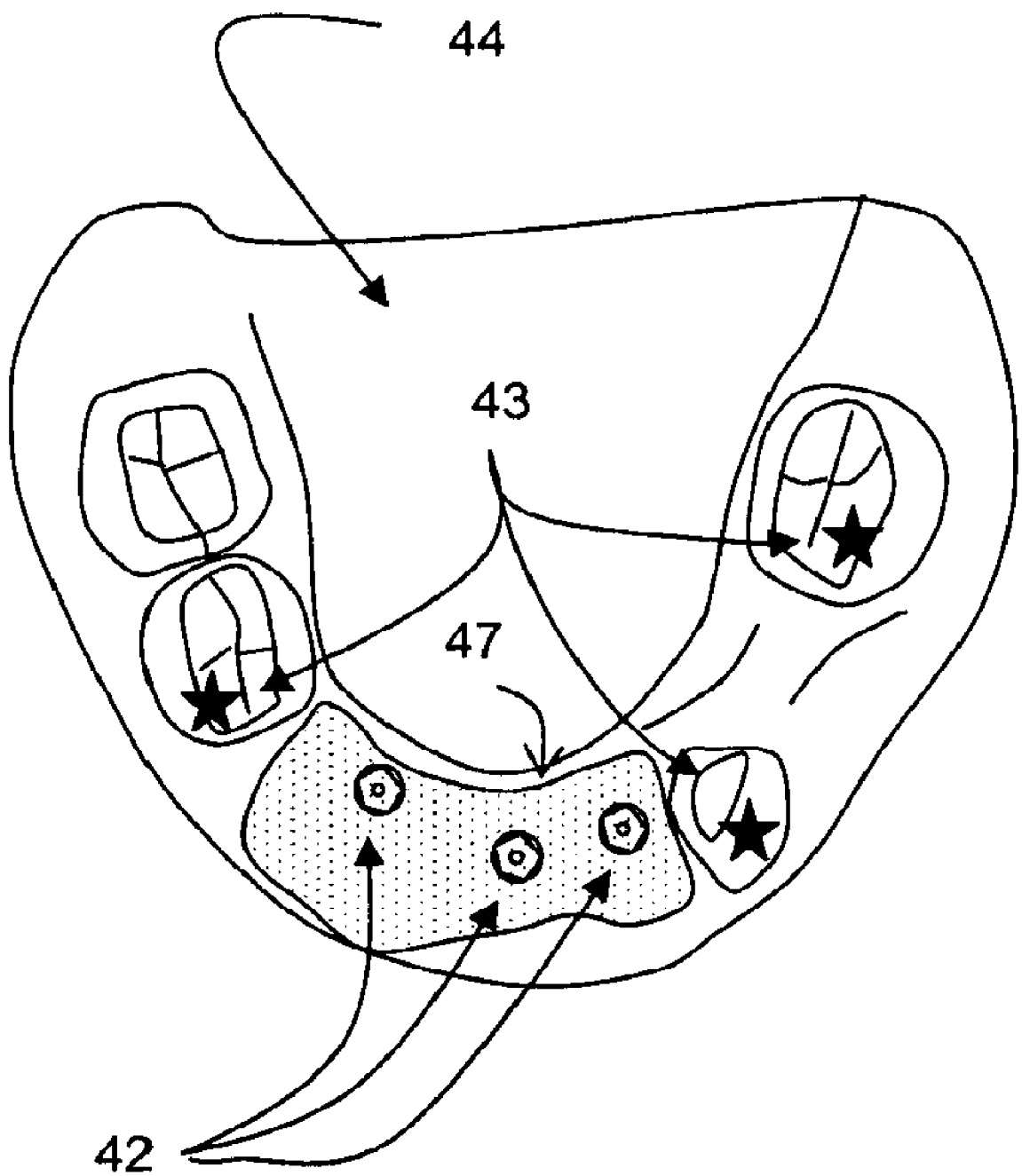
FIG. 9 is an illustration of the lower virtual cast prepared for anterior implants bone reduction.

FIG. 9 illustrates the virtual model of the lower cast 44 with the cast reshaped (as indicated by the reference numeral 47) to provide space for the restoration and to have the proper contour for the dental implants 42. Areas of contact for the occlusal index 56 are indicated by the stars identified by the reference numeral 43. In addition, FIG. 9 shows that some of the images of the original patient's teeth have been re-added or have not been virtually removed. These virtual teeth may be used as reference points for creating the first virtual drill guide and may provide a stable base for the actual first drill guide after it is formed. FIG. 9 also shows virtual dental implants 42 placed in the lower jaw in areas that have adequate volume of bone after the teeth are extracted.

The lower cast is positioned in the same computer space as the virtual model of the lower jaw 35 with dental implants 42. This step may occur when the virtual model of the lower jaw 35 includes radiographic scatter from metal elements in the patient's original teeth during the CT scan. For example, with radiographic scatter, the CT scan may still provide proper imaging of teeth roots, while the scanned dental casts may provide proper imaging of the teeth surfaces. By combining the scan of the dental casts with the CT scan of the patient's mouth and head, any radiographic scatter from the CT scan may be replaced by the scanned image of the dental cast, permitting a user technician to have a more clear image, thereby increasing the ability to properly place and align the implants. In the example of FIG. 9 contact areas 43 on the surface of three teeth have been retained to allow for proper indexing of the drill guide. Since the lower cast and the CT data about the lower jaw are oriented in computer space using the CT bite plate of FIG. 3, it is possible to create a drill guide that has contact on the teeth for proper orientation, a shape that determines the correct form of the bone 47, and that also has cylinders in it to determine the correct angulation and vertical position of the dental implants 42. One exemplary method for creating the virtual guide includes using an extrusion operation to create a mass formed to precisely interface with the virtual jaw and with the remaining virtual teeth of the virtual model.

Once the virtual drill guide's form and shape are determined, an actual drill guide may be manufactured by, for example, rapid prototyping or cutting with a five axis mill. In some embodiments, the guide is made from a block of methylmethacrylate resin with a 5 axis CNC mill. It can also be created by using a 5 axis mill to cut the depth and angulation of each implant guide hole in the dental cast and to then place metal guide tubes 52 in the correct angle and depth. The tubes can then be covered with autopolymerizing acrylic resin or vacuum formed plastic sheet to index them to the teeth.

Figure 10A:
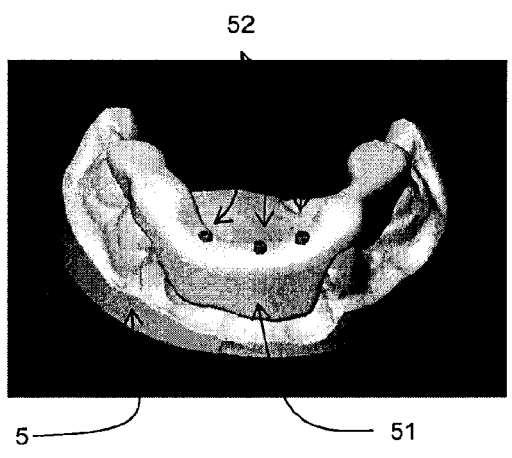
FIGS. 10A and 10B are images of a first drill guide.
Figure 11:
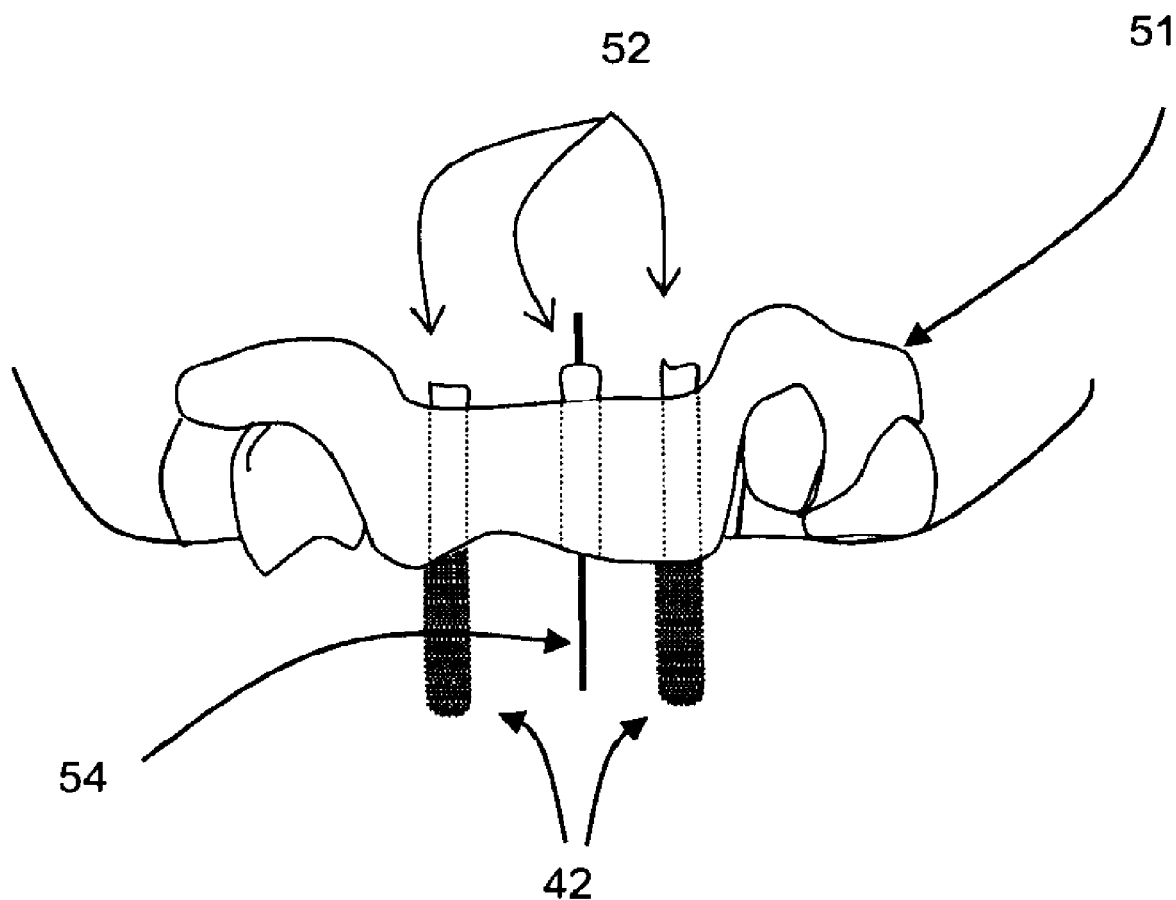
FIG. 11 is an illustration of the first drill guide resting on posterior teeth and the implant placement along with the guide pin in the anterior guide tube.

FIG. 10A illustrates the lower dental cast 5. The cast 5 may be mounted using its reference plate in a 5 axis mill and the cast may be cut using computer controlled milling to the same shape as the virtual contour of the lower jaw in the anterior area, where the first dental implants will be placed. As described below in FIG. 11, the first drill guide 51 may be used to place the anterior implants.

Figure 10B:
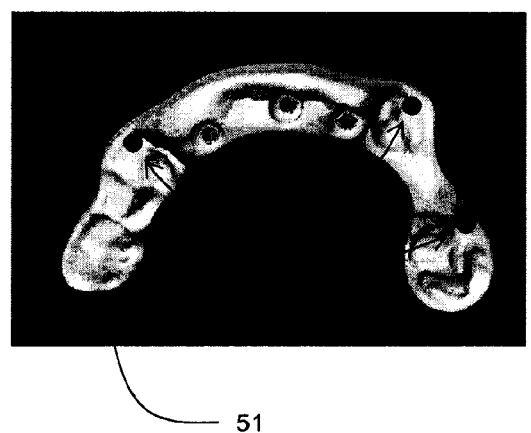

FIG. 10B illustrates the inside, or underside, of the first drill guide 51. The contour may be used to gauge the amount of bone that needs to be removed form the patient's jaw to have proper space for restorative material. This may be done by removing bone until the first drill guide correctly fits into the patient's mouth. As indicated by the numeral 53, the first drill guide may be shaped to rest on three cusp tips of the remaining teeth.

FIG. 11 illustrates the first drill guide 51 in use within the patient's mouth. The first drill guide 51 may be used to place two or more implants 42 and a central guide pin 54. First, the surgeon places the first drill guide 51 in the patient's mouth on the patient's posterior teeth and shapes the jaw bone until the guide 51 seats on the cusps of the posterior teeth. Next the metal tubes 52 in the guide 51 are used to drill holes in the jaw bone at the proper angulation and depth. Actual dental implants 42 may be placed in two or more of the drill sites. A guide pin 54 may be placed in one of the tubes to record the orientation of the first drill guide, and to be used as a reference for a second drill guide. In FIG. 11, the shaded part of the implant 42 represent the portion of the implant imbedded within the jaw bone.

Figure 12:
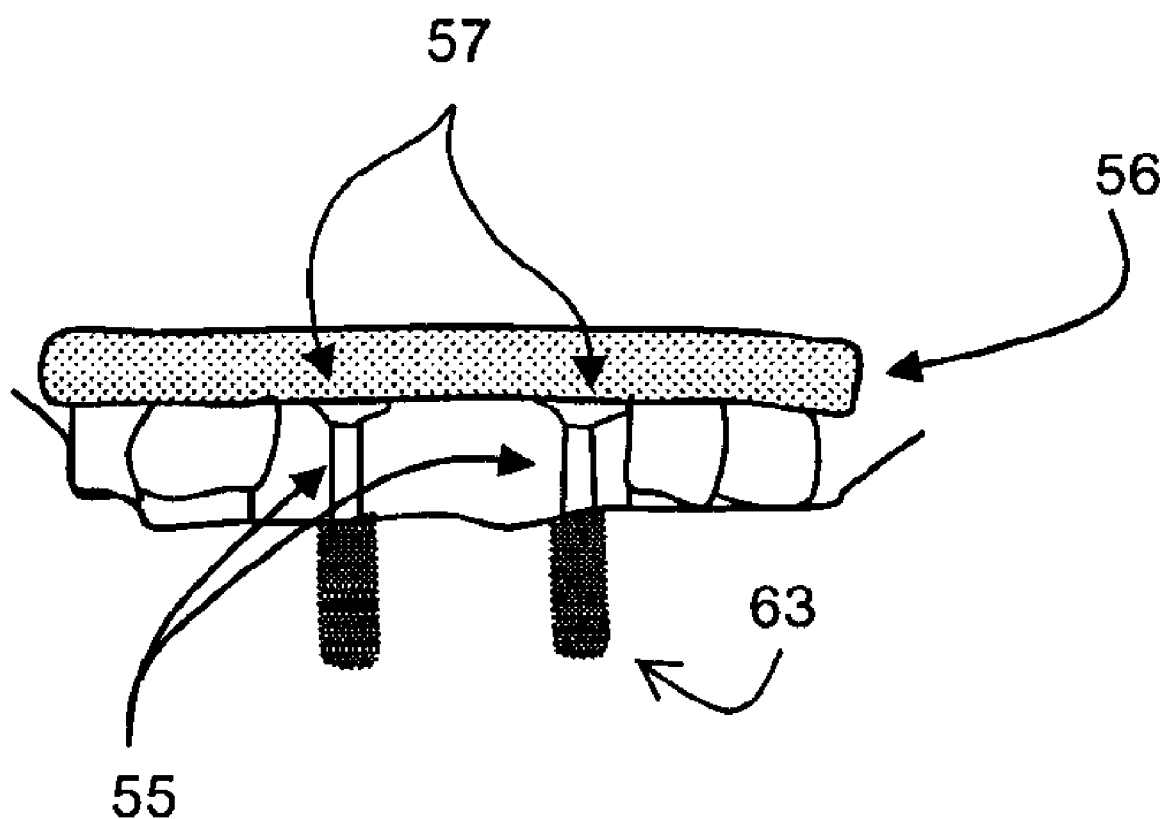
FIG. 12 is an illustration of an exemplary occlusal index used to record the position of two anterior dental implants.

FIG. 12 illustrates the position of two implants 42 in the patient's lower jaw 35 and an occlusal index 56 resting in place on the patient's remaining lower teeth. Impression copings 55 are attached to the top of the implants 42 then luted with light cured resin 57 to the index 56. As explained above, the occlusal index 56 may be shaped to fit both the upper cast and lower cast, and may be formed using scan data from the dental casts. Use of this index may eliminate the need for guiding the patient into any specific jaw position during surgery and also may eliminate the need for using soft tissue to index the correct position for the immediate load prosthesis.

FIG. 13 illustrates the index 56 placed on the upper dental cast 6 which is precisely oriented by attaching the upper mounting plate 9 in the same positional relationship to the lower mounting plate 8 as was required to make the virtual index. Next, the implant laboratory analogs 58 of the dental implants are attached to the impression copings 55 and luted as shown by the numeral 57 to the lower mounting plate 8 with light cured resin or cyanocrylate cement. This records the precise positional relationship of the anterior dental implants relative to the lower mounting plate 8 and the planned immediate load prosthesis and the immediate upper denture. By locating the index 56 relative to the cast teeth of the upper dental cast 6, the positional relationship of the lower dental implants relative to the lower guide plate 8 can be determined. This tracks the position of bite of the lower jaw relative to the upper jaw, helping avoid excessive displacement.

Figure 14A:
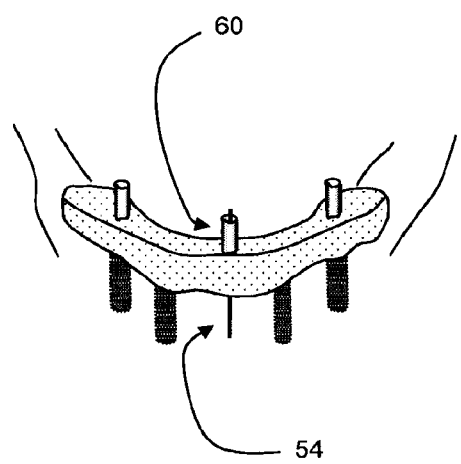
FIGS. 14A and 14B are illustrations respectively showing a second drill guide held in position with the guide pin and all the lower implants indexed with impression copings.

FIG. 14A illustrates an actual second drill guide 60 in place on the actual lower jaw 35. Here, all the remaining lower teeth have been extracted and the anterior guide pin 54 has been placed in an anterior guide tube 61 to position the second drill guide 60 in the same spatial relationship as the first drill guide 51. The second drill guide 60 is made in a manner similar to the first. This includes, among other steps described above, removing the remaining virtual teeth and introducing virtual implants into the virtual model. The second virtual drill guide 60 may be formed on the virtual model using, for example, an extrusion technique or operation to have an inner surface that precisely meets up with the remaining surface of the virtual jaw bone. Once formed virtually, the actual second drill guide may be machined or otherwise formed as described above.

The lower cast may be cut with, for example, a 5 axis mill to match the shape of the virtual mandible after the virtual teeth have been virtually removed and the bone reshaped for restorative space. The actual second drill guide 60 may be made with rapid prototyping, milling a piece of methylmetacrylate resin or making the guide on the cast by drilling the guide holes with a 5 axis mill and inserting the metal tubes. The tubes may then be incorporated in autopolymerizing acrylic resin or vacuum formed plastic, processes well known in the laboratory art. This machined dental cast, that now matches the virtual mandible, may be used by the surgeon at the time of surgery to confirm what he or she is doing and as a model, outside the mouth, that he or she may look at and reference.

Once the second drill guide is formed, the patient's posterior teeth may be removed and the patient's bone may be formed so that the second drill guide properly fits on the patient's jaw. The second drill guide may then be introduced to the patient's mouth, orienting the second drill guide so that the guide pin acts as reference. Using the second drill guide, the surgeon may place the remaining implants, such as the posterior dental implants. After the posterior implants have been placed, the anterior drill hole is used to guide the position of the anterior dental implant. The guide tubes provide precise information about the angle and depth of the dental implant but this system also allows for the ability to change the position of the implants at the time of surgery if required.

Figure 14B:
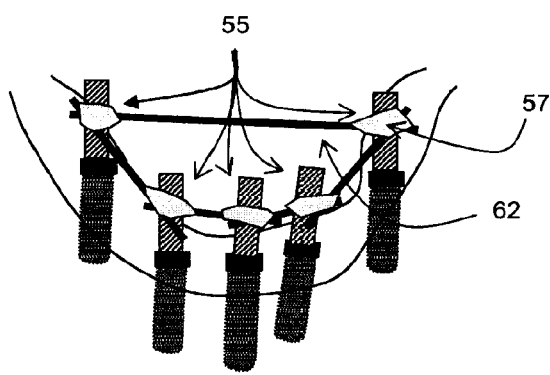

FIG. 14B illustrates indexing of the position of all the lower implants with impression copings 55 in the patient's mouth. In this example, each coping 55 is luted to the adjacent coping with a metal rod 62 and light cured resin 57 or a suitable luting medium. Accordingly, the position of each coping is fixed relative to all other copings. Note that if one of the implants is in a position different than was planned, the indexing process will record the new position of the implant.

Figure 15:
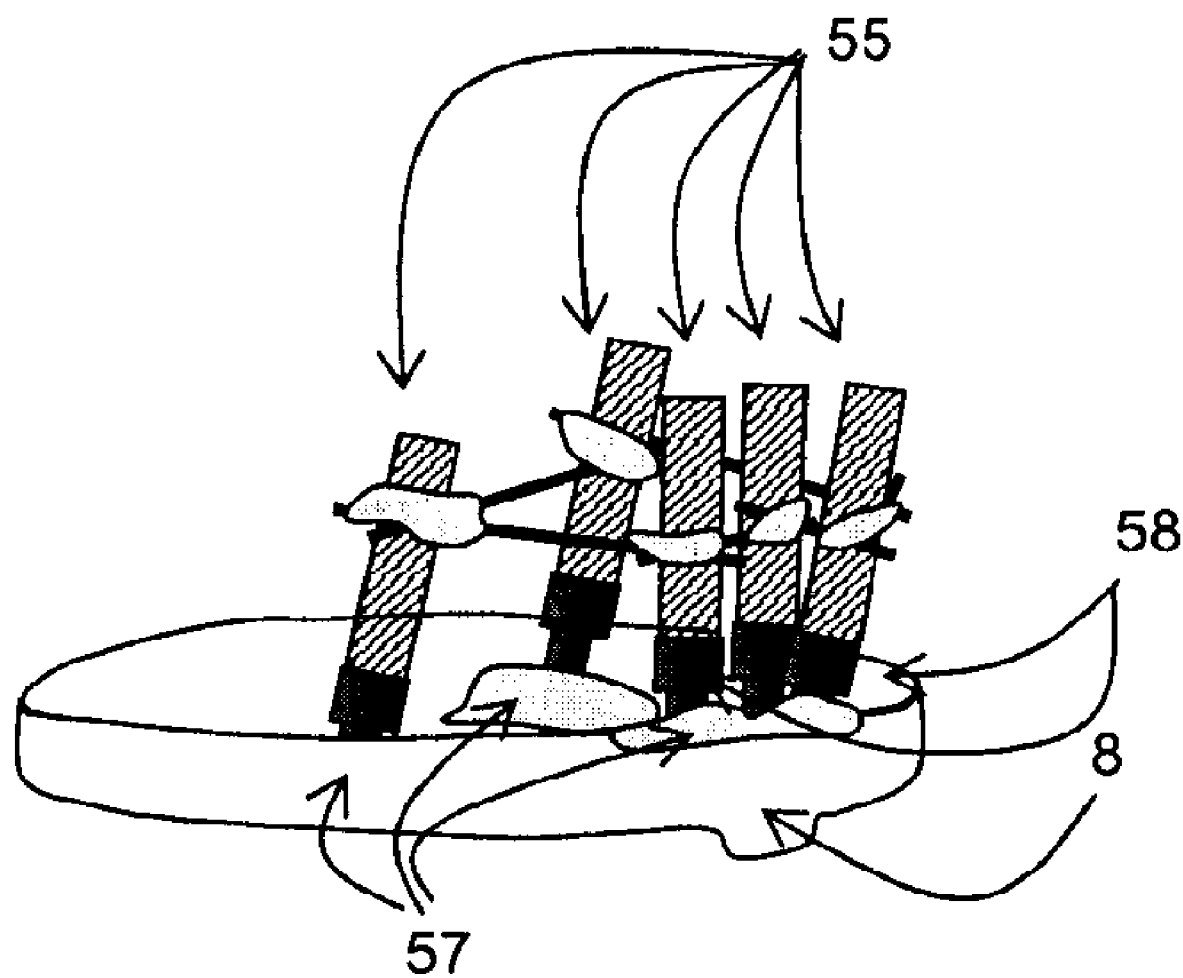
FIG. 15 is an illustration of two anterior analogues joined to the index of all the implants. The remaining laboratory implant analogues are luted to the lower mounting plate.

FIG. 15 illustrates the indexed copings 55 attached to the previously placed two laboratory implant analogues 58 that were positioned on the mounting plate 8 with the occlusal index 56 as described with reference to FIG. 13. The connection between the two previously placed implant analogues 58 and their associated copings assists in orienting all the connected copings 55 relative to the lower guide plate 8. The remaining laboratory analogues are then luted to the mounting plate with a suitable adhesive 57.

FIG. 16 illustrates an immediate load prosthesis 66 indexed to the upper mounting plate 9 using a stone occlusal index 65 milled, for example, from plaster. The spatial orientation of the upper mounting plate 9 to the immediate load prosthesis 66 is the same as the virtual plate in FIGS. 8B & 8C. The steps of imaging, positioning virtual denture teeth, milling the occlusal index and denture teeth are further disclosed in U.S. application Ser. No. 11/739,310, titled, Computer Machined Dental Tooth System and Method, filed Apr. 24, 2007. The process disclosed therein also may be used to position and manufacture the upper immediate denture and the lower immediate load prosthesis 66. The occlusal index 65 is used to hold the immediate load prosthesis 66 in proper orientation relative to the lower mounting plate 8 so that autopolymerizing acrylic resin can be used to join temporary cylinders 69 to the prosthesis. This is a common practice in the dental art. All of the mentioned steps can be preformed by a laboratory technician outside the mouth to save time and improve quality.

Figure 17:
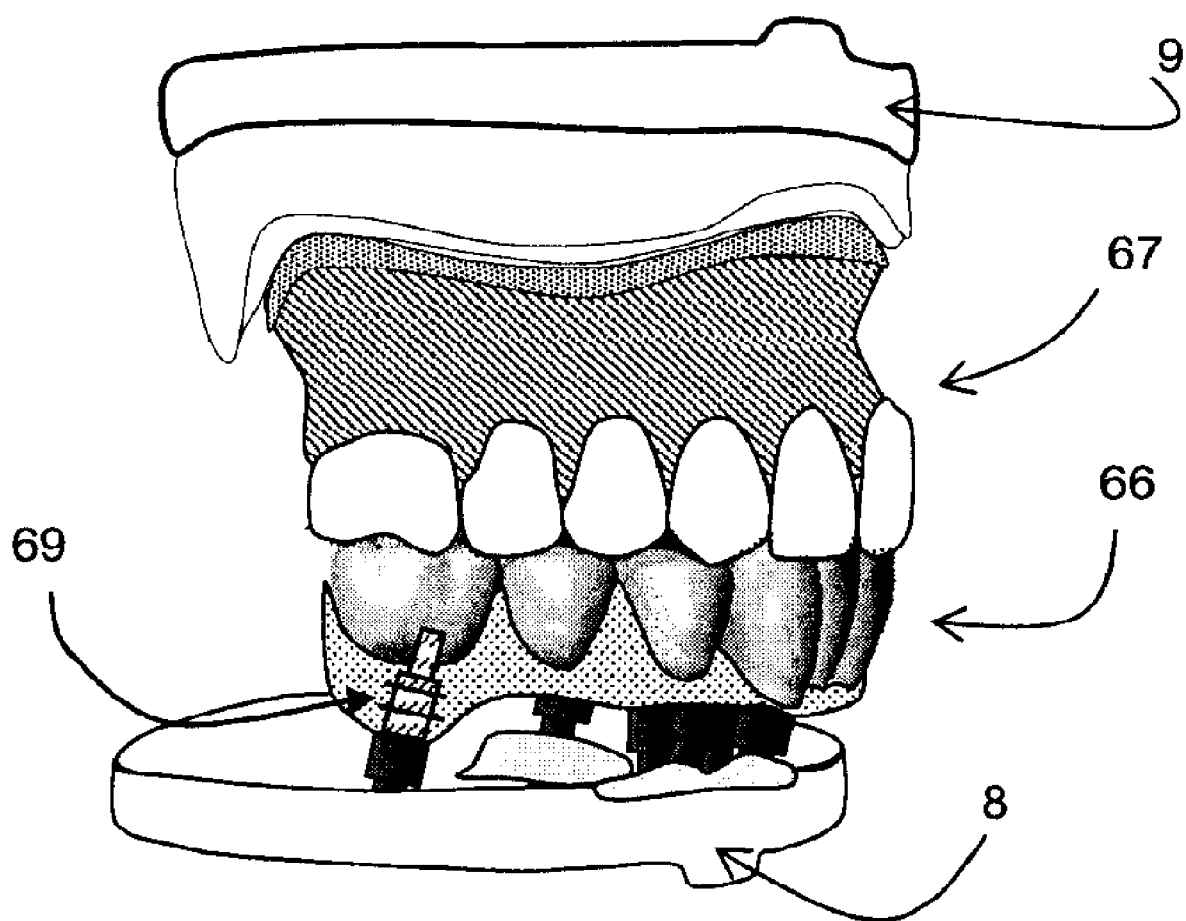
FIG. 17 is an illustration of an upper immediate denture and the lower immediate load prosthesis ready to be inserted in the patient's mouth at the time of surgery.

FIG. 17 illustrates the upper immediate denture 67 and the lower immediate load prosthesis 66 ready for insertion in the patient's mouth. The immediate load prosthesis 66 is attached to the previously installed lower implants with titanium or gold screws at the time of surgery. This fixes the lower prosthesis in place. Since the spatial orientation of the dental casts and mounting plates are recorded and reproduced with digital imaging, and since the indexes and guides are computer milled, the precision of the esthetic and occlusal orientation of the prosthesis can be predictably produced at the time of surgery.

Figure 18:
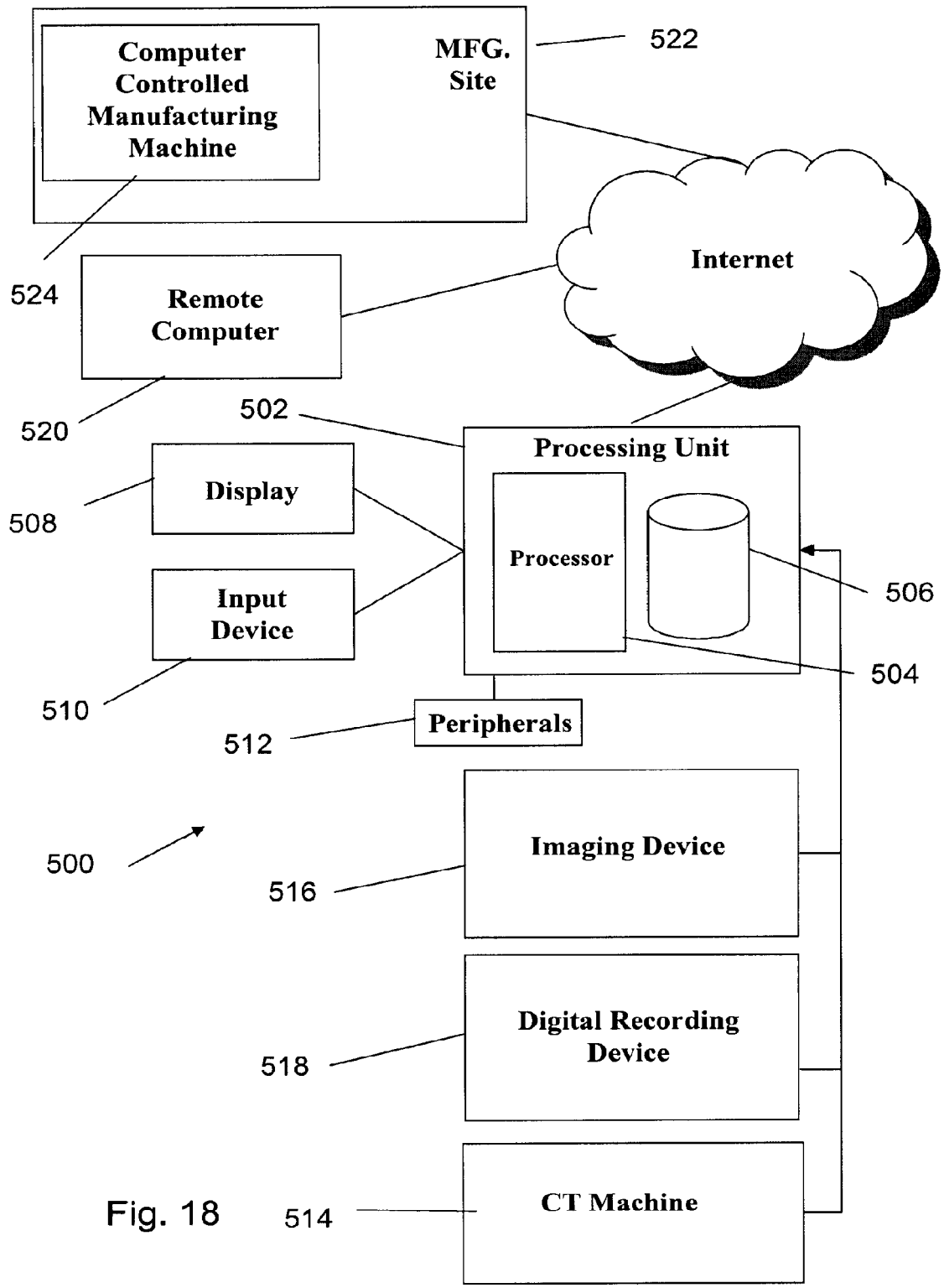
FIG. 18 is a block diagram of an exemplary system usable to accomplish the methods disclosed herein.

An exemplary system for performing the processes and methods described herein is shown in FIG. 18. FIG. 18 includes a computer system 500 including a processing unit 502 containing a processor 504 and a memory 506. An output device, such as a display 508 and input devices 510, such as keyboards, scanners, and others, are in communication with the processing unit 502. Additional peripheral devices 512 also may be present.

The processor 504 may for example be a microprocessor of a known type. The memory 506 may, in some embodiments, collectively represents two or more different types of memory. For example, the memory 506 may include a read only memory (ROM) that stores a program executed by the processor 504, as well as static data for the processor 504. In addition, the memory 506 may include some random access memory (RAM) that is used by the processor 504 to store data that changes dynamically during program execution. The processor 504 and the memory 506 could optionally be implemented as respective portions of a known device that is commonly referred to as a microcontroller. The memory 506 may contain one or more executable programs to carry out the methods contained herein, including joining, separating, storing, and other actions including Boolean actions.

The system 500 also may include a CT machine 514, an imaging device 516, and a digital recorder 518. These may be any of the CT machines, imaging devices, and digital recorders described herein. Data from the CT machine 514, the imaging device 516, and the digital recorder 518 may be accessed by the processing unit 502 and used to carry out the processes and methods disclosed. Data may be communicated to the processing unit 502 by any known method, including by direct communication, by storing and physically delivering, such as using a removable disc, removable drive, or other removable storage device, over e-mail, or using other known transfer systems over a network, such as a LAN or WAN, including over the internet or otherwise. Any data received at the processing unit 502 may be stored in the memory 506 for processing and manipulation by the processor 504. In some embodiments, the memory 506 is a storage database separate from the processor 504.

As shown, the processing unit 502 is connected to a WAN, disclosed herein as the Internet. Using the Internet, the processing unit 502 can communicate data, including .stl files showing modeled data for manufacture to either a remote computer 520 or a manufacturing site 522, which in this embodiment includes a computer controlled manufacturing machine 524, which may be, for example, an NC mill or layered manufacturing machine. Other machines also are contemplated. Using the Internet, data may be sent from the processing unit 502 to the remote computer 520 or the manufacturing site 522. In one example, the remote computer may be a dentist's or other provider's computer. Using the remote computer, the provider may access the images on the processing unit 502 (or alternatively receive and store a local copy) and may modify or edit the images as desired. Once edits or modifications are made the revised data may be sent back to the processing unit 502, or alternatively, may be sent directly to the manufacturing site. Once the manufacturing site 522 receives the data, it may be used to program the computer controller manufacturing machine 524 to create the intra oral devices. In some embodiments, the manufacturing site is in the 522 is in the same building or in the same room as the processing unit 502, and communication need not occur over the Internet.

In one exemplary aspect, the present disclosure is directed to a method of creating a surgical drill guide. The method includes the steps of generating a virtual model of a portion of a patient's jaw and introducing virtual dental implants to the virtual model. It also includes generating a virtual drill guide shaped to fit on the virtual jaw, the virtual drill guide indicating the position of the virtual dental implants, and manufacturing an actual drill guide based on data of the virtual drill guide.

In some aspects, generating a virtual model includes scanning a portion of a patient's jaw to obtain scan data; and generating a 3-D image of the portion of the patient's jaw. In one aspect, the method includes shaping the virtual model of the patient's jaw. This may include removing jaw material that overlaps with virtual denture teeth, and may include shaping the virtual jaw to permit restorative materials to be added therein. In one aspect, the method may comprise virtually extracting at least one but less than all of the patient's virtual teeth from the virtual jaw, and wherein generating a virtual drill guide includes shaping the virtual drill guide to fit against at least one of the remaining teeth and against a surface of the portion of the patient's jaw. In one aspect, the method may include removing all the remaining patient's virtual teeth from the virtual jaw; introducing second virtual dental implants to the virtual model; generating a second virtual drill guide shaped to fit on the virtual jaw, the second virtual drill guide indicating the position of the second virtual dental implants; and manufacturing an actual second drill guide based on data of the second virtual drill guide. In one aspect, the portion of the patient's jaw includes virtual teeth corresponding to actual patient teeth, and the method comprises replacing at least one virtual tooth of the virtual teeth with a virtual denture tooth; and virtually removing portions of the virtual jaw to provide space to fit restorative material between the virtual denture tooth and the portion of the patient's jaw. In one aspect, manufacturing an actual drill guide includes transferring code based on the virtual drill guide to a CNC mill; and milling the actual drill guide on a CNC mill. In one aspect, the method includes scanning a dental cast to obtain scan data; and replacing at least one virtual tooth of the virtual teeth with a virtual tooth generated from the scan data.

In yet another exemplary aspect, this disclosure is directed to a method of aligning a patient's bite position. The method may comprise generating a virtual model of an upper jaw with upper teeth and a lower jaw with lower teeth of a patient; creating a virtual index between the upper teeth and the lower teeth, the virtual index having indentations shaped to fit the upper teeth and lower teeth of the patient, and indicating a bite position of the lower jaw relative to the upper jaw of the virtual model; manufacturing an actual index based on data of the virtual index; arranging the actual index in place on at least one tooth of the actual upper or lower teeth in the patient's mouth; affixing impression copings to the actual index, the impression copings identifying positions of in-place dental implants; and tracking a bite position of the actual lower jaw relative to the upper jaw using the impression copings and the actual index.

In one aspect, the method comprises implanting the actual dental implants in the patient's jaw bone; and placing the impression copings on the actual dental implants. In one aspect, tracking a bite position includes: removing the actual index and impression copings from the mouth and orienting the actual index and the impression copings relative to a cast of one of the patient's upper teeth or lower teeth; and attaching the impression copings to a mounting plate in a manner that positions the actual index in a location that makes the bite position of the lower jaw relative to the upper jaw substantially similar to the bite position of the virtual model. In one aspect, creating a virtual index between the upper teeth and the lower teeth of the patient includes form fitting the index about the upper teeth and the lower teeth of the patient. In one aspect, manufacturing an actual index comprises: transferring code based on the virtual index to a CNC mill; and milling the actual index on a CNC mill. In one aspect, affixing impression copings to the actual index includes luting with one of a light cured resin and a cement.

In another exemplary aspect, the present disclosure is directed to a method of implanting dental implants. The method comprises removing at least one first tooth from a patient's jaw; placing a first surgical drill guide in the patient's mouth, the first surgical drill guide being oriented relative to at least one second tooth in the patient's jaw; drilling a bore in the patient's jaw using the first surgical drill guide; removing the at least one second tooth from the patient's jaw; inserting a guide pin in the bore; placing a second surgical drill guide in the patient's mouth, the second surgical drill guide being oriented relative to the guide pin in the bore; and implanting a dental implant based on the position of the second surgical drill guide.

In one aspect, removing at least one first tooth includes removing an anterior tooth and wherein removing the at least one second tooth includes removing a posteriorly located tooth. In one aspect, the first drill guide is positioned based on the relative position of at least three other teeth. In one aspect, the method includes inserting at least two dental implants using the first surgical drill guide. In one aspect, the method comprises: removing the guide pin from the bore; and inserting a dental implant into the bore. In one aspect, the method comprises generating a first virtual surgical drill guide and a second virtual surgical drill guide based on a virtual image of the patient's jaw. In one aspect, the method comprises manufacturing the first surgical drill guide and the second surgical drill guide based on data representative of the respective first and second virtual drill guides. In one aspect, manufacturing the first drill guide includes: transferring code based on the first virtual drill guide to a CNC mill; and milling the drill guide on a CNC mill. In one aspect, the method comprises inserting metal tubes into holes in the milled guide. In one aspect, the method comprises: removing bone tissue from the jaw to provide space for restorative materials; and using the first surgical drill guide as a reference to determine whether the bone tissue removed is a sufficient amount. In one aspect, using the first surgical drill guide as a reference includes removing jaw bone tissue until the first surgical guide rests on three cusp tips of teeth.

In another exemplary aspect, the present disclosure is directed to a method of aligning a patient's bite position. The method may include inserting at least one first dental implant in a patient's mouth; orienting a first impression coping on the first dental implant; arranging an occlusal index in place on at least one tooth of actual upper or lower teeth in the patient's mouth; affixing the first impression coping to the occlusal index, the impression coping identifying the relative position of the at least one first dental implant; removing the actual index and the affixed first impression coping from the mouth; inserting at least on second dental implant in the patient's mouth; orienting a second impression coping on the at least one second dental implant; orienting a third impression coping on the at least one first dental implant; and rigidly connecting the second and third impression copings to identify the position of the second dental implant relative to the first dental implant.

In one exemplary aspect, the method includes orienting the occlusal index and the affixed first impression coping relative to a dental cast of one of the patient's upper teeth or lower teeth. In one aspect, the method includes attaching a first implant laboratory analog to the first impression coping and affixing it in a location that indicates the position of the first dental implant relative to the dental cast. In one aspect, the method includes removing the first impression coping from the first implant laboratory analog; attaching a second implant laboratory analog to the second impression coping; and orienting the third impression coping on the first implant laboratory analog; and affixing the second implant laboratory analog at a location that indicates the position of the second dental implant relative to the first dental implant.

Although the discussion of the exemplary method disclosed herein is primarily directed to creating a dental prosthesis to replace the lower teeth and jaw, it should be understood that the method may be equally applicable to creating a prosthesis for the upper teeth and jaw. Further, it is contemplated that the method may be used to create prostheses for replacing teeth of both the lower and upper jaws.

Although several selected embodiments have been illustrated and described in detail, it will be understood that they are exemplary, and that a variety of substitutions and alterations are possible without departing from the spirit and scope of the present invention, as defined by the following claims. Further, it is contemplated that features disclosed in any one embodiment, system, or method may be used on any other embodiment, system, or method.

What is claimed:

1. A method of creating a surgical drill guide, comprising:
    generating a virtual model of a portion of a patient's jaw, said virtual model comprising a virtual jaw and virtual teeth;
    shaping the virtual model;
    virtually extracting at least one but less than all of the virtual teeth from the virtual model, thus leaving one or more remaining virtual teeth;
    introducing virtual dental implants to the virtual model;
    generating a virtual drill guide shaped to fit on the virtual jaw, the virtual drill guide indicating the position of the virtual dental implants, wherein said generating a virtual drill guide includes shaping the virtual drill guide to fit against at least one of the remaining virtual teeth and against a surface of the portion of the patient's jaw; and
    manufacturing an actual drill guide based on data of the virtual drill guide.

2. The method of claim 1, wherein said generating a virtual model includes:
    scanning a portion of the patient's jaw to obtain scan data; and
    generating a 3-D image of the portion of the patient's jaw.

3. The method of claim 1, wherein said shaping the virtual model includes removing jaw material that overlaps with virtual denture teeth.

4. The method of claim 1, wherein said shaping the virtual model includes shaping the virtual jaw to permit restorative materials to be added therein.

5. The method of claim 1, including removing all the remaining virtual teeth from the virtual jaw;
    introducing second virtual dental implants to the virtual model;
    generating a second virtual drill guide shaped to fit on the virtual jaw, the second virtual drill guide indicating the position of the second virtual dental implants; and
    manufacturing an actual second drill guide based on data of the second virtual drill guide.

6. The method of claim 1, wherein the portion of the patient's jaw includes virtual teeth corresponding to actual patient teeth, the method comprising:
    replacing at least one virtual tooth of the virtual teeth with a virtual denture tooth; and
    virtually removing portions of the virtual jaw to provide space to fit restorative material between the virtual denture tooth and the portion of the patient's jaw.

7. The method of claim 1, wherein said manufacturing an actual drill guide includes:
    transferring code based on the virtual drill guide to a CNC mill; and
    milling the actual drill guide on a CNC mill.

8. The method of claim 1, including
    scanning a dental cast to obtain scan data; and
    replacing at least one virtual tooth of the virtual teeth with a virtual tooth generated from the scan data.

* * * * *